US009303109B2

(12) United States Patent
Greco

(10) Patent No.: US 9,303,109 B2
(45) Date of Patent: Apr. 5, 2016

(54) CATALYST SYSTEMS CONTAINING BORON-BRIDGED CYCLOPENTADIENYL-FLUORENYL METALLOCENE COMPOUNDS WITH AN ALKENYL SUBSTITUENT

(71) Applicant: Chevron Phillips Chemical Company LP, The Woodlands, TX (US)

(72) Inventor: Jeffrey F. Greco, Tulsa, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/533,161

(22) Filed: Nov. 5, 2014

(65) Prior Publication Data
US 2015/0141599 A1    May 21, 2015

Related U.S. Application Data

(60) Provisional application No. 61/905,894, filed on Nov. 19, 2013.

(51) Int. Cl.
| | | |
|---|---|---|
| C08F 4/6592 | (2006.01) | |
| C08F 4/642 | (2006.01) | |
| C08F 210/16 | (2006.01) | |
| C08L 23/08 | (2006.01) | |
| C08F 110/02 | (2006.01) | |
| C08F 10/02 | (2006.01) | |
| C08F 4/659 | (2006.01) | |

(52) U.S. Cl.
CPC .......... *C08F 210/16* (2013.01); *C08F 4/65927* (2013.01); *C08F 10/02* (2013.01); *C08F 110/02* (2013.01); *C08L 23/0815* (2013.01); *C08F 4/65904* (2013.01); *C08F 4/65912* (2013.01); *C08F 4/65916* (2013.01)

(58) Field of Classification Search
CPC ............. C08F 4/65927; C08F 4/65912; C08F 4/65916; C08F 210/16
See application file for complete search history.

(56) References Cited

U.S. PATENT DOCUMENTS

| | | |
|---|---|---|
| 3,242,099 A | 3/1966 | Manyik |
| 3,248,179 A | 4/1966 | Norwood |
| 4,501,885 A | 2/1985 | Sherk |
| 4,588,790 A | 5/1986 | Jenkins |
| 4,794,096 A | 12/1988 | Ewen |
| 4,808,561 A | 2/1989 | Welborn |
| 5,155,186 A | 10/1992 | Hogan et al. |
| 5,352,749 A | 10/1994 | DeChellis |
| 5,436,304 A | 7/1995 | Griffin |
| 5,455,314 A | 10/1995 | Burns |
| 5,565,175 A | 10/1996 | Hottovy |
| 5,575,979 A | 11/1996 | Hanson |
| 5,576,259 A | 11/1996 | Hasegawa |
| 5,739,220 A | 4/1998 | Shamshoum et al. |
| 5,807,938 A | 9/1998 | Kaneko |
| 5,919,983 A | 7/1999 | Rosen |
| 6,107,230 A | 8/2000 | McDaniel |
| 6,165,929 A | 12/2000 | McDaniel |
| 6,239,235 B1 | 5/2001 | Hottovy |
| 6,262,191 B1 | 7/2001 | Hottovy |
| 6,291,601 B1 | 9/2001 | Debras |
| 6,294,494 B1 | 9/2001 | McDaniel |
| 6,300,271 B1 | 10/2001 | McDaniel |
| 6,316,553 B1 | 11/2001 | McDaniel |
| 6,355,594 B1 | 3/2002 | McDaniel |
| 6,376,415 B1 | 4/2002 | McDaniel |
| 6,384,139 B1 | 5/2002 | Ho et al. |
| 6,388,017 B1 | 5/2002 | McDaniel |
| 6,391,816 B1 | 5/2002 | McDaniel |
| 6,395,666 B1 | 5/2002 | McDaniel |
| 6,399,707 B1 | 6/2002 | Meka et al. |
| 6,455,660 B1 | 9/2002 | Clutton et al. |
| 6,500,949 B2 | 12/2002 | Campbell, Jr. et al. |
| 6,524,987 B1 | 2/2003 | Collins |
| 6,548,441 B1 | 4/2003 | McDaniel |
| 6,548,442 B1 | 4/2003 | Collins |
| 6,576,583 B1 | 6/2003 | McDaniel |
| 6,613,712 B1 | 9/2003 | McDaniel |
| 6,632,894 B1 | 10/2003 | McDaniel |
| 6,667,274 B1 | 12/2003 | Hawley |
| 6,750,302 B1 | 6/2004 | McDaniel |

(Continued)

FOREIGN PATENT DOCUMENTS

| | | | |
|---|---|---|---|
| WO | WO 97/33921 A1 | 9/1997 | |
| WO | WO 98/54260 A1 | 12/1998 | |

(Continued)

OTHER PUBLICATIONS

Ashe A J et al.: "The CS_Symmetric Aminoboranediyl-Bridged Zirconocene Dichloride A(ETA-9-C13H8)-BN(IPR)2(ETA-C5H4) UZRCL2: Its Synthesis, Structure, and Behavior as an Olefin Polymerization Catalyst", Organometallics, ACS, Washington, DC, US, vol. 23, No. 9, Apr. 26, 2004, p. 2197-2200.

Vahid Karimkhani et al.: "Revisiting the long-chain branch formation mechanism in metallocene catalyzed polyethylenes", Polymer Chemistry, vol. 4, No. 13, Jan. 1, 2013, p. 3774-3790.

International Search Report and the Written Opinion of the International Searching Authority in PCT/US2014/064128 dated Feb. 25, 2015, 9 pages.

*Modern Plastics Encyclopedia*, Mid-Nov. 1995 Issue, vol. 72, No. 12, 3 pages.

*Film Extrusion Manual—Process, Materials, Properties*, TAPPI Press, 1992, 16 pages.

(Continued)

*Primary Examiner* — Caixia Lu
(74) *Attorney, Agent, or Firm* — Merchant & Gould P.C.

(57) ABSTRACT

Disclosed herein are catalyst compositions containing boron-bridged, cyclopentadienyl-fluorenyl metallocene compounds with an alkenyl substituent. These catalyst compositions can be used for the polymerization of olefins. For example, ethylene copolymers produced using these catalyst compositions can be characterized by a combination of a flat or a conventional comonomer distribution and low levels of long chain branching.

19 Claims, 6 Drawing Sheets

(56) References Cited

U.S. PATENT DOCUMENTS

| | | | |
|---|---|---|---|
| 6,833,415 | B2 | 12/2004 | Kendrick |
| 6,891,004 | B2 | 5/2005 | Arai et al. |
| 7,026,494 | B1 | 4/2006 | Yang et al. |
| 7,226,886 | B2 | 6/2007 | Jayaratne et al. |
| 7,294,599 | B2 | 11/2007 | Jensen et al. |
| 7,312,283 | B2 | 12/2007 | Martin et al. |
| 7,321,015 | B2 | 1/2008 | Hoang et al. |
| 7,517,939 | B2 | 4/2009 | Yang et al. |
| 7,601,665 | B2 | 10/2009 | McDaniel et al. |
| 7,619,047 | B2 | 11/2009 | Yang et al. |
| 7,829,646 | B2 | 11/2010 | DesLauriers et al. |
| 7,884,163 | B2 | 2/2011 | McDaniel et al. |
| 8,114,946 | B2 | 2/2012 | Yang et al. |
| 8,153,043 | B2 | 4/2012 | Krishnaswamy et al. |
| 8,288,487 | B2 | 10/2012 | Yang et al. |
| 8,309,485 | B2 | 11/2012 | Yang et al. |
| 8,383,754 | B2 | 2/2013 | Yang et al. |
| 8,389,615 | B2 | 3/2013 | Tse et al. |
| 8,546,499 | B2 | 10/2013 | Garroff et al. |
| 8,623,973 | B1 | 1/2014 | McDaniel et al. |
| 8,703,886 | B1 | 4/2014 | Yang et al. |
| 2001/0025115 | A1* | 9/2001 | Campbell, Jr. .......... C07F 17/00 556/7 |
| 2003/0149180 | A1 | 8/2003 | Van Dun et al. |
| 2003/0199650 | A1* | 10/2003 | Devore ................... C07F 17/00 526/160 |
| 2004/0059070 | A1 | 3/2004 | Whitte et al. |
| 2006/0189769 | A1 | 8/2006 | Hoang et al. |
| 2009/0264607 | A1 | 10/2009 | Terreur et al. |
| 2010/0227989 | A1 | 9/2010 | Yang et al. |
| 2012/0088890 | A1 | 4/2012 | Buck et al. |
| 2012/0316298 | A1 | 12/2012 | Razavi |
| 2015/0141593 | A1 | 5/2015 | Greco |
| 2015/0141597 | A1 | 5/2015 | Greco |
| 2015/0141598 | A1 | 5/2015 | Greco |

FOREIGN PATENT DOCUMENTS

| | | |
|---|---|---|
| WO | WO 00/20462 | 4/2000 |
| WO | WO 2012/069574 A1 | 5/2012 |
| WO | WO 2013/078351 A1 | 5/2013 |

OTHER PUBLICATIONS

Hieber et al., "Some Correlations Involving the Sear Viscosity of Polystyrene Melts," *Rheol. Acta*, 28, (1989), pp. 321-332.

Hieber et al., "Shear-Rate-Dependence Modeling of Polymer Melt Viscosity," *Polym. Eng. Sci.*, (1992), vol. 32, pp. 931-938.

R. B. Bird, et al., *Dynamics of Polymeric Liquids, vol. 1, Fluid Mechanics*, 2nd Edition, John Wiley & Sons (1987), 3 pages.

Janzen et al., entitled "Diagnosing Long-Chain Branching in Polyethylenes," *J. Mol. Struct.*, 485-486, 569-584 (1999), 20 pages.

Wyatt, Philip J., entitled "Light Scattering and the Absolute Characterization of Macromolecules," *Analytica Chimica Acta*, 272 (1993), pp. 1-40.

Arnett, et al., "Zero-Shear Viscosity of Some Ethyl Branched paraffinic Model Polymers," *J. Phys. Chem.* (1980), vol. 84, No. 6, pp. 649-652.

Yu, et al. entitled "Long Chain Branches in Metallocene-Catalyzed Polyethylene Determined by a Combination of SEC/Multi-Angle Light Scattering, NMR and Rheology," *Polymer Preprint*, (2003), 2 pages.

Ashe, III, et al., entitled "Aminoboranediyl-Bridged Zirconocenes: Highly Active Olefin Polymerization Catalysts," Organometallics 1999, 18, pp. 2288-2290.

Biswas et al., "Chemical Modification of Metallocene-Based Polyethylene-Octene Elastomer Through Solution Grafting of Acrylic Acid and its Effect on the Physico-Mechanical Properties"; Published online May 30, 2007 in Wiley InterScience (www.interscience.wiley.com); Journal of Applied Polymer Science, vol. 105, 3409-3417; © 2007 Wiley Periodicals, Inc.

Braunschweig et al., entitled "Sterically Demanding Hetero-Substituted [2]Borametallocenophanes of Group IV Metals: Synthesis, Structure and Reactivity," Chem. Eur. J. 2011, 17, pp. 12101-12107.

Braunschweig et al., entitled "Synthesis and Structure of Amionbis($\eta$-cyclopentadienyl)boranes and Related Compounds," Journal of Organometallics Chemistry 619 (2001), pp. 305-312.

Braunschweig et al., entitled, Synthesis and Structure of [1]Borametallocenophanes of Titanium, Zirconium, and Hafnium, Eur. J. Inorg. Chem. 1999, pp. 1899-1904.

Burns, et al., entitled Stable Borate-Bridged *ansa*-Zirconocene Completes. Preparation and X-ray Crystallographic Characterization of [CP*$_2$Al]+[Me(Ph)B($\eta^5$-C$_5$H$_4$)$_2$ZrCl$_2$]- and [PPN]+[Cl(Ph)B($\eta^5$-C$_5$H$_4$)$_2$ZrCl$_2$], Organometallics 1999, 18, pp. 5432-5434.

Haggin, Group Notation Revised in Periodic Table; Feb. 4, 1985; C&EN; 2 pgs.

Lai et al., "Fracture Behaviors of Metallocene-Catalyzed Polyethylene Elastomer via Peroxide Crosslinking"; Published online May 21, 2009 in Wiley InterScience (www.interscience.wiley.com); Journal of Applied Polymer Science, vol. 113, 3791-3798 © 2009 Wiley Productions.

Lai et al., "Fracture Behaviors of Metallocene-Catalyzed Polyethylene Elastomer via Silane Crosslinking"; Published online in Wiley InterScience (www.interscience.wiley.com); Journal of Applied Polymer Science, vol. 101, 2472-2481 © 2006 Wiley Productions.

Lai et al., "Melt Mixed Polypropylene/Metallocene Polyethylene Thermoplastic Elastomer Nanocomposites: Part I: Effect of Silane Modification"; Journal of Macromolecular Science, Copyright © Taylor & Francis Group, LLC, 2012, 16 pgs.

Reetz, et al., entitled "Donor Complexes of bis (1-indenyl) phenylborane dichlorozirconium as Isospecific Catalysts in Propene Polymerization," Chem. Commun., 1999, pp. 1105-1106.

Shapiro, Pamela J., entitled "Boron-Bridged Group-4 *ansa*-Metallocene Complexes," Eur. J. Inorg. Chem. 2001, pp. 321-326.

International Search Report and the Written Opinion of the International Searching Authority in PCT/US2014/065255 dated May 28, 2015, 9 pages.

* cited by examiner

CATALYST SYSTEMS CONTAINING BORON-BRIDGED CYCLOPENTADIENYL-FLUORENYL METALLOCENE COMPOUNDS WITH AN ALKENYL SUBSTITUENT

REFERENCE TO RELATED APPLICATION

This application claims the benefit of U.S. Provisional Application Ser. No. 61/905,894, filed on Nov. 19, 2013, the disclosure of which is incorporated herein by reference in its entirety.

BACKGROUND OF THE INVENTION

Polyolefins such as high density polyethylene (HDPE) homopolymer and linear low density polyethylene (LLDPE) copolymer can be produced using various combinations of catalyst systems and polymerization processes. In some end-use applications, it can be beneficial for the polymer to have a combination of a flat or a conventional comonomer distribution and low levels of long chain branching. Moreover, it can be beneficial for the catalyst system employed to facilitate good incorporation of a comonomer during polymerization, as well as easy control of the molecular weight distribution with the addition of hydrogen during polymerization. Accordingly, it is to these ends that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to new catalyst compositions, methods for preparing the catalyst compositions, methods for using the catalyst compositions to polymerize olefins, the polymer resins produced using such catalyst compositions, and articles produced using these polymer resins. In particular, the present invention relates to boron-bridged metallocene compounds containing an alkenyl substituent, and to catalyst compositions employing such metallocene compounds. Catalyst compositions of the present invention that contain these boron-bridged metallocene compounds can be used to produce, for example, ethylene-based homopolymers and copolymers.

In accordance with an aspect of the present invention, disclosed and described herein are boron-bridged metallocene compounds having the formula:

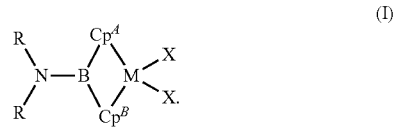

(I)

In formula (I), M can be Ti, Zr, or Hf; each X independently can be a monoanionic ligand; $Cp^A$ can be a cyclopentadienyl group with an alkenyl substituent; $Cp^B$ can be a fluorenyl group; and each R independently can be H, a $C_1$ to $C_{36}$ hydrocarbyl group, or a $C_1$ to $C_{36}$ hydrocarbylsilyl group.

Catalyst compositions containing the boron-bridged metallocene compounds of formula (I) also are provided by the present invention. In one aspect, a catalyst composition is disclosed which comprises a boron-bridged metallocene compound of formula (I) and an activator. Optionally, this catalyst composition can further comprise a co-catalyst, such as an organoaluminum compound. In some aspects, the activator can comprise an activator-support, while in other aspects, the activator can comprise an aluminoxane compound, an organoboron or organoborate compound, an ionizing ionic compound, or combinations thereof.

The present invention also contemplates and encompasses olefin polymerization processes. Such processes can comprise contacting a catalyst composition with an olefin monomer and optionally an olefin comonomer in a polymerization reactor system under polymerization conditions to produce an olefin polymer. Generally, the catalyst composition employed can comprise any of the boron-bridged metallocene compounds disclosed herein and any of the activators disclosed herein. Further, organoaluminum compounds or other co-catalysts also can be utilized in the catalyst compositions and/or polymerization processes.

Polymers produced from the polymerization of olefins, resulting in homopolymers, copolymers, terpolymers, etc., can be used to produce various articles of manufacture.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DEFINITIONS

Figure 1:
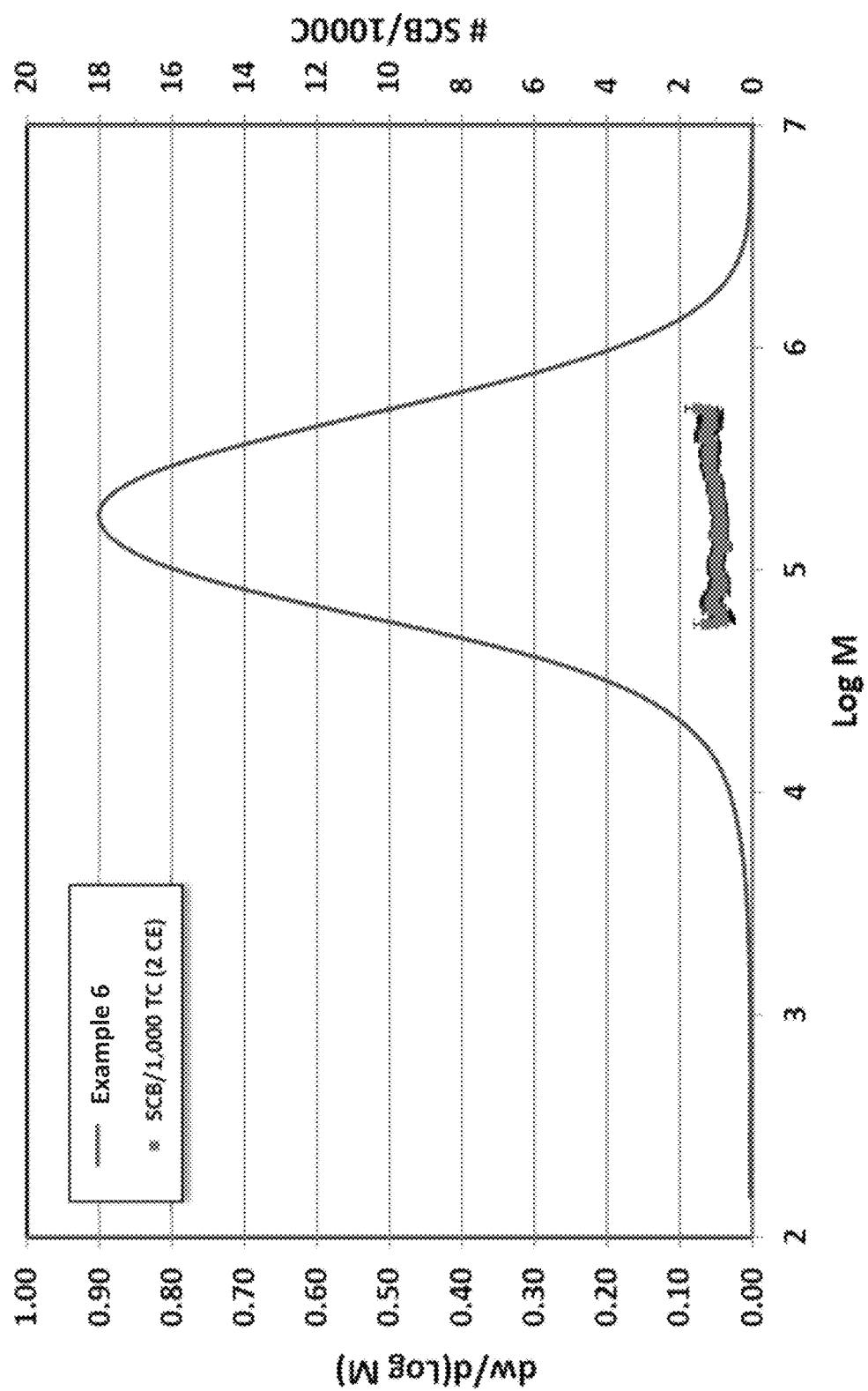
FIG. 1 presents a plot of the molecular weight distribution and short chain branch distribution of the polymer of Example 6.
Figure 2:
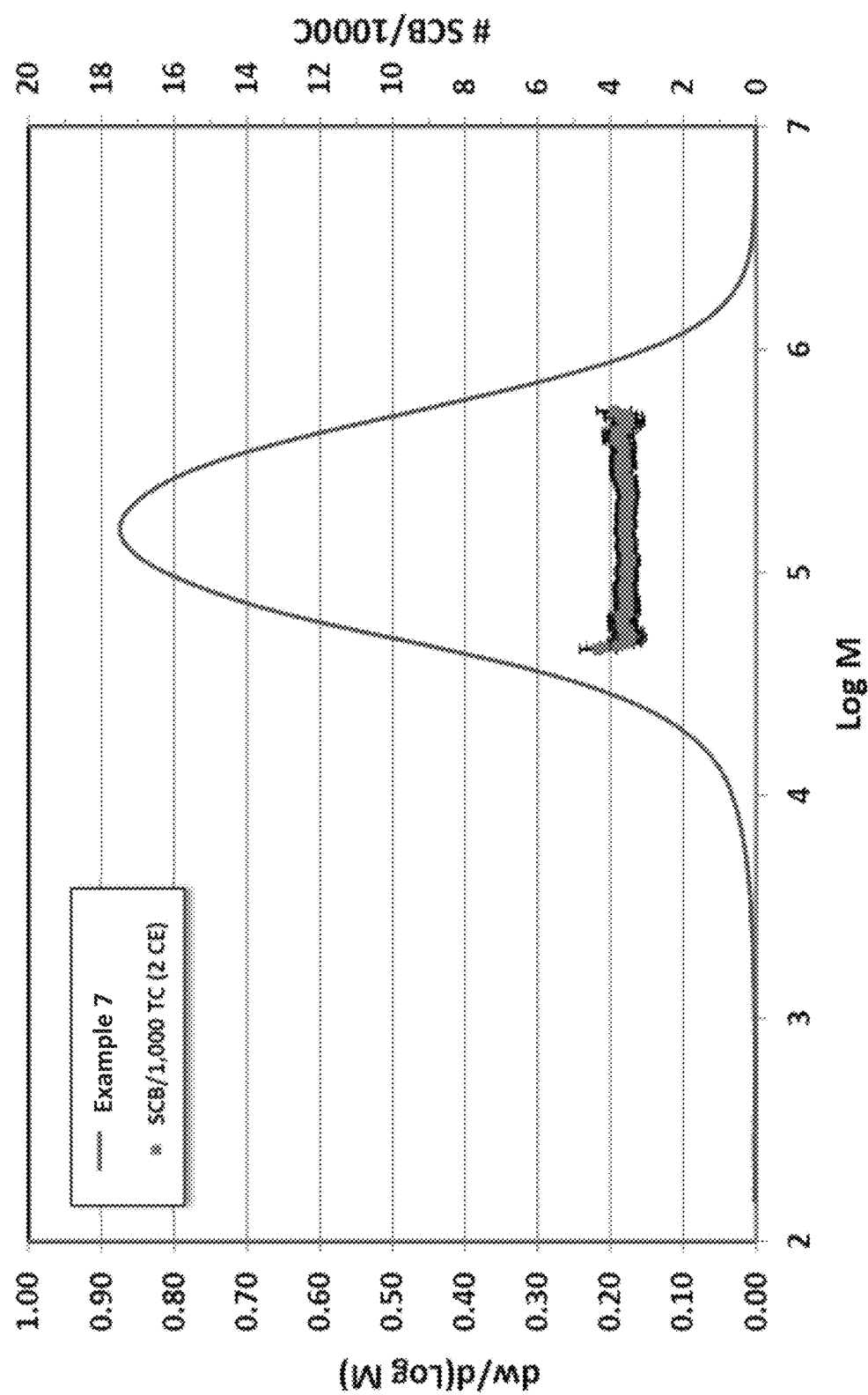
FIG. 2 presents a plot of the molecular weight distribution and short chain branch distribution of the polymer of Example 7.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of; (i) a boron-bridged metallocene compound, (ii) an activator, and (iii) optionally, a co-catalyst.

The terms "a," "an," "the," etc., are intended to include plural alternatives, e.g., at least one, unless otherwise specified. For instance, the disclosure of "an activator-support" or "a metallocene compound" is meant to encompass one, or mixtures or combinations of more than one, activator-support or metallocene compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer can be categorized an as ethylene/1-hexene copolymer.

In like manner, the scope of the term "polymerization" includes homopolymerization, copolymerization, terpolymerization, etc. Therefore, a copolymerization process can involve contacting one olefin monomer (e.g., ethylene) and one olefin comonomer (e.g., 1-hexene) to produce a copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used, for example, in addition to an activator-support. The term "co-catalyst" is used regardless of the actual function of the compound or any chemical mechanism by which the compound may operate.

The terms "chemically-treated solid oxide," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The "activator-support" of the present invention can be a chemically-treated solid oxide. The terms "support" and "activator-support" are not used to imply these components are inert, and such components should not be construed as an inert component of the catalyst composition. The term "activator," as used herein, refers generally to a substance that is capable of converting a metallocene component into a catalyst that can polymerize olefins, or converting a contact product of a metallocene component and a component that provides an activatable ligand (e.g., an alkyl, a hydride) to the metallocene, when the metallocene compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "metallocene" as used herein describes compounds comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands may include H, therefore this invention comprises ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. In some contexts, the metallocene is referred to simply as the "catalyst," in much the same way the term "co-catalyst" is used herein to refer to, for example, an organoaluminum compound.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the co-catalyst, the metallocene compound, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the polydispersity index, Mw/Mn, of an olefin polymer produced in an aspect of this invention. By a disclosure that the ratio of Mw/Mn can be in a range from about 2 to about 12, Applicants intend to recite that the Mw/Mn can be any ratio in the range and, for example, can be equal to about 2, about 3, about 4, about 5, about 6, about 7, about 8, about 9, about 10, about 11, or about 12. Additionally, the Mw/Mn can be within any range from about 2 to about 12 (for example, from about 2 to about 5), and this also includes any combination of ranges between about 2 and about 12 (for example, the Mw/Mn can be in a range from about 2 to about 4, or from about 6 to about 10). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

DETAILED DESCRIPTION OF THE INVENTION

The present invention is directed generally to new catalyst compositions, methods for preparing the catalyst compositions, methods for using the catalyst compositions to polymerize olefins, the polymer resins produced using such catalyst compositions, and articles produced using these polymer resins. In particular, the present invention relates to boron-bridged metallocene complexes containing an alkenyl substituent, to catalyst compositions employing these boron-bridged metallocene complexes, to polymerization processes utilizing such catalyst compositions, and to the resulting olefin polymers produced from the polymerization processes.

Boron-Bridged Metallocenes

The present invention discloses novel boron-bridged metallocene complexes or compounds containing an alkenyl substituent, and methods of making these complexes or compounds. In an aspect of this invention, the boron-bridged metallocene compound can have the formula:

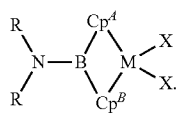

(I)

Within formula (I), M, $Cp^A$, $Cp^B$, each X, and each R are independent elements of the metallocene compound. Accordingly, the metallocene compound having formula (I) may be described using any combination of M, $Cp^A$, $Cp^B$, X, and R disclosed herein.

Unless otherwise specified, formula (I) above, any other structural formulas disclosed herein, and any metallocene complex, compound, or species disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In accordance with aspects of this invention, the metal in formula (I), M, can be Ti, Zr, or Hf. In one aspect, for instance, M can be Zr or Hf, while in another aspect, M can be Ti; alternatively, M can be Zr; or alternatively, M can be Hf.

Each X in formula (I) independently can be a monoanionic ligand. In some aspects, suitable monoanionic ligands can include, but are not limited to, H (hydride), $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^1_2$, or $-OSO_2R^1$, wherein $R^1$ is a $C_1$ to $C_{36}$ hydrocarbyl group. It is contemplated that each X can be either the same or a different monoanionic ligand.

In one aspect, each X independently can be H, $BH_4$, a halide (e.g., F, Cl, Br, etc.), a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. Alternatively, each X independently can be H, $BH_4$, a halide, $OBR^1_2$, or $OSO_2R^1$, wherein $R^1$ is a $C_1$ to $C_{18}$ hydrocarbyl group. In another aspect, each X independently can be H, $BH_4$, a halide, a $C_1$ to $C_{12}$ hydrocarbyl group, a $C_1$ to $C_{12}$ hydrocarboxy group, a $C_1$ to $C_{12}$ hydrocarbylaminyl group, a $C_1$ to $C_{12}$ hydrocarbylsilyl group, a $C_1$ to $C_{12}$ hydrocarbylaminylsilyl group, $OBR^1_2$, or $OSO_2R^1$, wherein $R^1$ is a $C_1$ to $C_{12}$ hydrocarbyl group. In another aspect, each X independently can be H, $BH_4$, a halide, a $C_1$ to $C_{10}$ hydrocarbyl group, a $C_1$ to $C_{10}$ hydrocarboxy group, a $C_1$ to $C_{10}$ hydrocarbylaminyl group, a $C_1$ to $C_{10}$ hydrocarbylsilyl group, a $C_1$ to $C_{10}$ hydrocarbylaminylsilyl group, $OBR^1_2$, or $OSO_2R^1$, wherein $R^1$ is a $C_1$ to $C_{10}$ hydrocarbyl group. In yet another aspect, each X independently can be H, $BH_4$, a halide, a $C_1$ to $C_8$ hydrocarbyl group, a $C_1$ to $C_8$ hydrocarboxy group, a $C_1$ to $C_8$ hydrocarbylaminyl group, a $C_1$ to $C_8$ hydrocarbylsilyl group, a $C_1$ to $C_8$ hydrocarbylaminylsilyl group, $OBR^1_2$, or $OSO_2R^1$, wherein $R^1$ is a $C_1$ to $C_8$ hydrocarbyl group. In still another aspect, each X independently can be a halide or a $C_1$ to $C_{18}$ hydrocarbyl group. For example, both X's can be Cl.

The hydrocarbyl group which can be an X (one or both) in formula (I) can be a $C_1$ to $C_{36}$ hydrocarbyl group, including, but not limited to, a $C_1$ to $C_{36}$ alkyl group, a $C_2$ to $C_{36}$ alkenyl group, a $C_4$ to $C_{36}$ cycloalkyl group, a $C_6$ to $C_{36}$ aryl group, or a $C_7$ to $C_{36}$ aralkyl group. For instance, each X independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, each X independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, each X independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, each X independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be an X in formula (I) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be an X in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be an X in formula (I) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, each X in formula (I) independently can be an ethenyl group, a propenyl group, a butenyl group, a pentenyl group, a hexenyl group, a heptenyl group, an octenyl group, a nonenyl group, or a decenyl group, while in another aspect, each X in formula (I) independently can be an ethenyl group, a propenyl group, a butenyl group, a pentenyl group, or a hexenyl group. For example, an X can be an ethenyl group; alternatively, a propenyl group; alternatively, a butenyl group; alternatively, a pentenyl group; or alternatively, a hexenyl group. In yet another aspect, an X can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

Each X in formula (I) independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, an X in formula (I) can be a cyclopentyl group, a substituted cyclopentyl group, a cyclohexyl group, or a substituted cyclohexyl group. Moreover, each X in formula (I) independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be an X in formula (I).

In some aspects, the aryl group which can be an X in formula (I) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be an X in formula (I).

In an aspect, the substituted phenyl group which can be an X in formula (I) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be an X in formula (I).

In some aspects, the aralkyl group which can be an X in formula (I) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be an X in formula (I).

In an aspect, each non-hydrogen substituent(s) for the substituted cycloalkyl group, substituted aryl group, or substituted aralkyl group which can be an X in formula (I) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be an X in formula (I). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be an X in formula (I) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be an X in formula (I) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be an X in formula (I) can comprise up to about 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be an X in formula (I) can be, for instance, a methylaminyl group (—$NHCH_3$), an ethylaminyl group (—$NHCH_2CH_3$), an n-propylaminyl group (—$NHCH_2CH_2CH_3$), an iso-propylaminyl group (—$NHCH(CH_3)_2$), an n-butylaminyl group (—$NHCH_2CH_2CH_2CH_3$), a t-butylaminyl group (—$NHC(CH_3)_3$), an n-pentylaminyl group (—$NHCH_2CH_2CH_2CH_2CH_3$), a neo-pentylaminyl group (—$NHCH_2C(CH_3)_3$), a phenylaminyl group (—$NHC_6H_5$), a tolylaminyl group (—$NHC_6H_4CH_3$), or a xylylaminyl group (—$NHC_6H_3(CH_3)_2$); alternatively, a methylaminyl group; alternatively, an ethylaminyl group; alternatively, a propylaminyl group; or alternatively, a phenylaminyl group. In other aspects, the hydrocarbylaminyl group which can be an X in formula (I) can be, for instance, a dimethylaminyl group (—$N(CH_3)_2$), a diethylaminyl group (—$N(CH_2CH_3)_2$), a di-n-propylaminyl group (—$N(CH_2CH_2CH_3)_2$), a di-iso-propylaminyl group (—$N(CH(CH_3)_2)_2$), a di-n-butylaminyl group (—$N(CH_2CH_2CH_2CH_3)_2$), a di-t-butylaminyl group (—$N(C(CH_3)_3)_2$), a di-n-pentylaminyl group (—$N(CH_2CH_2CH_2CH_2CH_3)_2$), a di-neo-pentylaminyl group (—$N(CH_2C(CH_3)_3)_2$), a di-phenylaminyl group (—$N(C_6$ H$_5$)$_2$), a di-tolylaminyl group (—N(C$_6$H$_4$CH$_3$)$_2$), or a di-xylylaminyl group (—N(C$_6$H$_3$(CH$_3$)$_2$)$_2$); alternatively, a dimethylaminyl group; alternatively, a di-ethylaminyl group; alternatively, a di-n-propylaminyl group; or alternatively, a di-phenylaminyl group.

In accordance with some aspects disclosed herein, each X independently can be a C$_1$ to C$_{36}$ hydrocarbylsilyl group; alternatively, a C$_1$ to C$_{24}$ hydrocarbylsilyl group; alternatively, a C$_1$ to C$_{18}$ hydrocarbylsilyl group; or alternatively, a C$_1$ to C$_8$ hydrocarbylsilyl group. In an aspect, each hydrocarbyl (one or more) of the hydrocarbylsilyl group can be any hydrocarbyl group disclosed herein (e.g., a C$_1$ to C$_5$ alkyl group, a C$_2$ to C$_5$ alkenyl group, a C$_5$ to C$_8$ cycloalkyl group, a C$_6$ to C$_8$ aryl group, a C$_7$ to C$_8$ aralkyl group, etc.). As used herein, hydrocarbylsilyl is intended to cover (mono)hydrocarbylsilyl (—SiH$_2$R), dihydrocarbylsilyl (—SiHR$_2$), and trihydrocarbylsilyl (—SiR$_3$) groups, with R being a hydrocarbyl group. In one aspect, the hydrocarbylsilyl group can be a C$_3$ to C$_{36}$ or a C$_3$ to C$_{18}$ trihydrocarbylsilyl group, such as, for example, a trialkylsilyl group or a triphenylsilyl group. Illustrative and non-limiting examples of hydrocarbylsilyl groups which can be an X in formula (I) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

A hydrocarbylaminylsilyl group is used herein to refer to groups containing at least one hydrocarbon moiety, at least one N atom, and at least one Si atom. Illustrative and non-limiting examples of hydrocarbylaminylsilyl groups which can be an X include, but are not limited to, —N(SiMe$_3$)$_2$, —N(SiEt$_3$)$_2$, and the like. Unless otherwise specified, the hydrocarbylaminylsilyl groups which can be an X can comprise up to about 36 carbon atoms (e.g., C$_1$ to C$_{36}$, C$_1$ to C$_{18}$, C$_1$ to C$_{12}$, or C$_1$ to C$_8$ hydrocarbylaminylsilyl groups). In an aspect, each hydrocarbyl (one or more) of the hydrocarbylaminylsilyl group can be any hydrocarbyl group disclosed herein (e.g., a C$_1$ to C$_5$ alkyl group, a C$_2$ to C$_5$ alkenyl group, a C$_5$ to C$_8$ cycloalkyl group, a C$_6$ to C$_8$ aryl group, a C$_7$ to C$_8$ aralkyl group, etc.). Moreover, hydrocarbylaminylsilyl is intended to cover —NH(SiH$_2$R), —NH(SiHR$_2$), —NH(SiR$_3$), —N(SiH$_2$R)$_2$, —N(SiHR$_2$)$_2$, and —N(SiR$_3$)$_2$ groups, among others, with R being a hydrocarbyl group.

In an aspect, each X independently can be —OBR$^1_2$ or —OSO$_2$R$^1$, wherein R$^1$ is a C$_1$ to C$_{36}$ hydrocarbyl group, or alternatively, a C$_1$ to C$_{18}$ hydrocarbyl group. The hydrocarbyl group in OBR$^1_2$ and/or OSO$_2$R$^1$ independently can be any hydrocarbyl group disclosed herein, such as, for instance, a C$_1$ to C$_{18}$ alkyl group, a C$_2$ to C$_{18}$ alkenyl group, a C$_4$ to C$_{18}$ cycloalkyl group, a C$_6$ to C$_{18}$ aryl group, or a C$_7$ to C$_{18}$ aralkyl group; alternatively, a C$_1$ to C$_{12}$ alkyl group, a C$_2$ to C$_{12}$ alkenyl group, a C$_4$ to C$_{12}$ cycloalkyl group, a C$_6$ to C$_{12}$ aryl group, or a C$_7$ to C$_{12}$ aralkyl group; or alternatively, a C$_1$ to C$_8$ alkyl group, a C$_2$ to C$_8$ alkenyl group, a C$_5$ to C$_8$ cycloalkyl group, a C$_6$ to C$_8$ aryl group, or a C$_7$ to C$_8$ aralkyl group.

In one aspect, each X independently can be H, BH$_4$, a halide, or a C$_1$ to C$_{36}$ hydrocarbyl group, hydrocarboxy group, hydrocarbylaminyl group, hydrocarbylsilyl group, or hydrocarbylaminylsilyl group, while in another aspect, each X independently can be H, BH$_4$, or a C$_1$ to C$_{18}$ hydrocarboxy group, hydrocarbylaminyl group, hydrocarbylsilyl group, or hydrocarbylaminylsilyl group. In yet another aspect, each X independently can be a halide; alternatively, a C$_1$ to C$_{18}$ hydrocarbyl group; alternatively, a C$_1$ to C$_{18}$ hydrocarboxy group; alternatively, a C$_1$ to C$_{18}$ hydrocarbylaminyl group; alternatively, a C$_1$ to C$_{18}$ hydrocarbylsilyl group; or alternatively, a C$_1$ to C$_{18}$ hydrocarbylaminylsilyl group. In still another aspect, both X's can be H; alternatively, F; alternatively, Cl; alternatively, Br; alternatively, I; alternatively, BH$_4$; alternatively, a C$_1$ to C$_{18}$ hydrocarbyl group; alternatively, a C$_1$ to C$_{18}$ hydrocarboxy group; alternatively, a C$_1$ to C$_{18}$ hydrocarbylaminyl group; alternatively, a C$_1$ to C$_{18}$ hydrocarbylsilyl group; or alternatively, a C$_1$ to C$_{18}$ hydrocarbylaminylsilyl group.

Each X independently can be, in some aspects, H, a halide, methyl, phenyl, benzyl, an alkoxy, an aryloxy, acetylacetonate, formate, acetate, stearate, oleate, benzoate, an alkylaminyl, a dialkylaminyl, a trihydrocarbylsilyl, or a hydrocarbylaminylsilyl; alternatively, H, a halide, methyl, phenyl, or benzyl; alternatively, an alkoxy, an aryloxy, or acetylacetonate; alternatively, an alkylaminyl or a dialkylaminyl; alternatively, a trihydrocarbylsilyl or hydrocarbylaminylsilyl; alternatively, H or a halide; alternatively, methyl, phenyl, benzyl, an alkoxy, an aryloxy, acetylacetonate, an alkylaminyl, or a dialkylaminyl; alternatively, H; alternatively, a halide; alternatively, methyl; alternatively, phenyl; alternatively, benzyl; alternatively, an alkoxy; alternatively, an aryloxy; alternatively, acetylacetonate; alternatively, an alkylaminyl; alternatively, a dialkylaminyl; alternatively, a trihydrocarbylsilyl; or alternatively, a hydrocarbylaminylsilyl. In these and other aspects, the alkoxy, aryloxy, alkylaminyl, dialkylaminyl, trihydrocarbylsilyl, and hydrocarbylaminylsilyl can be a C$_1$ to C$_{36}$, a C$_1$ to C$_{18}$, a C$_1$ to C$_{12}$, or a C$_1$ to C$_8$ alkoxy, aryloxy, alkylaminyl, dialkylaminyl, trihydrocarbylsilyl, and hydrocarbylaminylsilyl.

Moreover, each X independently can be, in certain aspects, a halide or a C$_1$ to C$_{18}$ hydrocarbyl group; alternatively, a halide or a C$_1$ to C$_8$ hydrocarbyl group; alternatively, F, Cl, Br, I, methyl, benzyl, or phenyl; alternatively, Cl, methyl, benzyl, or phenyl; alternatively, a C$_1$ to C$_{18}$ alkoxy, aryloxy, alkylaminyl, dialkylaminyl, trihydrocarbylsilyl, or hydrocarbylaminylsilyl group; alternatively, a C$_1$ to C$_8$ alkoxy, aryloxy, alkylaminyl, dialkylaminyl, trihydrocarbylsilyl, or hydrocarbylaminylsilyl group; or alternatively, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

In formula (I), Cp$^A$ can be a cyclopentadienyl group with an alkenyl substituent, and Cp$^B$ can be a fluorenyl group. The alkenyl substituent can be at any suitable position(s) on Cp$^A$ that conforms to the rules of chemical valence. In some aspects, Cp$^A$ has only one substituent, and that one substituent is the alkenyl substituent.

In one aspect, the alkenyl substituent can be a C$_2$ to C$_{18}$ alkenyl group, i.e., any C$_2$ to C$_{18}$ alkenyl group disclosed herein. In another aspect, the alkenyl substituent can be an ethenyl group, a propenyl group, a butenyl group, a pentenyl group, a hexenyl group, a heptenyl group, an octenyl group, a nonenyl group, or a decenyl group. In yet another aspect, the alkenyl substituent can be a C$_2$ to C$_{12}$ linear or branched alkenyl group; alternatively, a C$_2$ to C$_8$ linear or branched alkenyl group; alternatively, a C$_3$ to C$_{12}$ linear alkenyl group; alternatively, a C$_2$ to C$_8$ linear alkenyl group; alternatively, a C$_2$ to C$_8$ terminal alkenyl group; or alternatively, a C$_3$ to C$_6$ terminal alkenyl group.

In accordance with non-limiting aspects of this invention, Cp$^A$ can be a cyclopentadienyl group with only an alkenyl substituent, and Cp$^B$ can be a fluorenyl group that does not contain any substituents; or Cp$^A$ can be a cyclopentadienyl group with an alkenyl substituent and one or more other substituents, and Cp$^B$ can be a fluorenyl group that does not contain an alkenyl substituent, but contains one or more other substituents; or Cp$^A$ can be a cyclopentadienyl group with an alkenyl substituent and one or more other substituents, and Cp$^B$ can be a fluorenyl group that does not contain any substituents; or Cp$^A$ can be a cyclopentadienyl group with only an alkenyl substituent, and Cp$^B$ can be a fluorenyl group that contains one or more substituents.

In some aspects, Cp$^A$ can contain a substituent (one or more) in addition to the alkenyl substituent, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. Similarly, $Cp^B$ can contain a substituent (one or more), e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. Hence, each substituent independently can be H; alternatively, a halide; alternatively, a $C_1$ to $C_{18}$ hydrocarbyl group; alternatively, a $C_1$ to $C_{18}$ halogenated hydrocarbyl group; alternatively, a $C_1$ to $C_{18}$ hydrocarboxy group; alternatively, a $C_1$ to $C_{18}$ hydrocarbylsilyl group; alternatively, a $C_1$ to $C_{12}$ hydrocarbyl group or a $C_1$ to $C_{12}$ hydrocarbylsilyl group; or alternatively, a $C_1$ to $C_8$ alkyl group or a $C_3$ to $C_8$ alkenyl group. The halide, $C_1$ to $C_{36}$ hydrocarbyl group, $C_1$ to $C_{36}$ hydrocarboxy group, and $C_1$ to $C_{36}$ hydrocarbylsilyl group which can be a substituent on $Cp^A$ and/or $Cp^B$ in formula (I) can be any halide, $C_1$ to $C_{36}$ hydrocarbyl group, $C_1$ to $C_{36}$ hydrocarboxy group, and $C_1$ to $C_{36}$ hydrocarbylsilyl group described herein (e.g., as pertaining to X in formula (I)). A substituent on $Cp^A$ and/or $Cp^B$ independently can be, in cer3tain aspects, a $C_1$ to $C_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

As a non-limiting example, each substituent on $Cp^A$ and/or $Cp^B$ independently can be H, $C_1$, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group (or other substituted aryl group), a benzyl group, a naphthyl group, a trimethylsilyl group, a triisopropylsilyl group, a triphenylsilyl group, an allyldimethylsilyl group, or a 1-methylcyclohexyl group; alternatively, H; alternatively, Cl; alternatively, $CF_3$; alternatively, a methyl group; alternatively, an ethyl group; alternatively, a propyl group; alternatively, a butyl group; alternatively, a pentyl group; alternatively, a hexyl group; alternatively, a heptyl group; alternatively, an octyl group, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; alternatively, a benzyl group; alternatively, a naphthyl group; alternatively, a trimethylsilyl group; alternatively, a triisopropylsilyl group; alternatively, a triphenylsilyl group; alternatively, an allyldimethylsilyl group; or alternatively, a 1-methylcyclohexyl group.

In one aspect, for example, each substituent on $Cp^A$ and/or $Cp^B$ independently can be H or a $C_1$ to $C_{18}$ hydrocarbyl group; alternatively, a $C_1$ to $C_{10}$ hydrocarbyl group; alternatively, a $C_1$ to $C_6$ linear or branched alkyl group (e.g., a tert-butyl group); alternatively, H, $C_1$, $CF_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, an allyldimethylsilyl group, or a 1-methylcyclohexyl group, and the like; alternatively, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group; alternatively, a methyl group, an ethyl group, a propyl group, a butyl group, a pentyl group, or a hexyl group; alternatively, a methyl group; alternatively, an ethyl group; alternatively, a propyl group; alternatively, a butyl group; or alternatively, a tert-butyl group.

In formula (I), each R independently can be H, a $C_1$ to $C_{36}$ hydrocarbyl group, or a $C_1$ to $C_{36}$ hydrocarbylsilyl group. The $C_1$ to $C_{36}$ hydrocarbyl group and $C_1$ to $C_{36}$ hydrocarbylsilyl group which can be a R in formula (I) can be any $C_1$ to $C_{36}$ hydrocarbyl group or $C_1$ to $C_{36}$ hydrocarbylsilyl group described herein (e.g., as pertaining to X in formula (I)). It is contemplated that each R can be either the same or a different substituent group. For example, each R independently can be H, a $C_1$ to $C_{18}$ hydrocarbyl group, or a $C_1$ to $C_{18}$ hydrocarbylsilyl group. In some aspects, each R independently can be a $C_1$ to $C_6$ linear or branched alkyl group (e.g., an isopropyl group). In other aspects, each R independently can be a methyl group, an ethyl group, a propyl group, a butyl group, a pentyl group, a hexyl group, a heptyl group, an octyl group, a nonyl group, a decyl group, a phenyl group, a tolyl group, a benzyl group, a naphthyl group, a trimethylsilyl group, a triisopropylsilyl group, a triphenylsilyl group, an allyldimethylsilyl group, or a 1-methylcyclohexyl group, and the like.

Illustrative and non-limiting examples of boron-bridged metallocene compounds with an alkenyl substituent can include the following compounds:

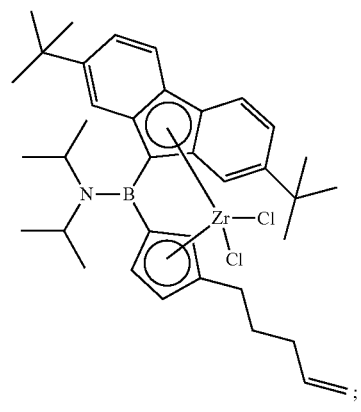

(MET-A)

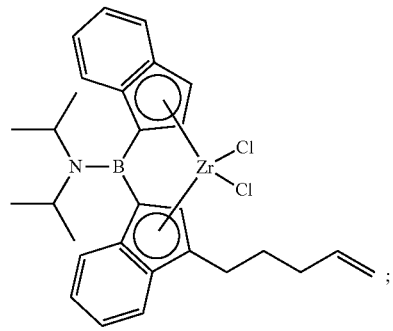

(MET-B)

and the like.

Methods of making boron-bridged metallocene complexes of the present invention also are encompassed herein. These metallocene complexes can be synthesized by various suitable procedures, such as those described in WO 00/20462, the disclosure of which is incorporated herein by reference in its entirety, and the procedures provided herein. A representative synthesis scheme is provided below, wherein the boron-bridged metallocene compound is synthesized in a multistep process from dichloro(diisopropylamino)borane.

Hence, in formula (A), $Cp^A$ can be a cyclopentadienyl group with an alkenyl substituent, $Cp^B$ can be a fluorenyl group, and each R independently can be H, or any $C_1$ to $C_{36}$ hydrocarbyl group or $C_1$ to $C_{36}$ hydrocarbylsilyl group disclosed herein.

Illustrative and non-limiting examples of cyclopentadienyl-indenyl boron-bridged ligand compounds (with the alkenyl substituent on the cyclopentadienyl group) can include the following compounds:

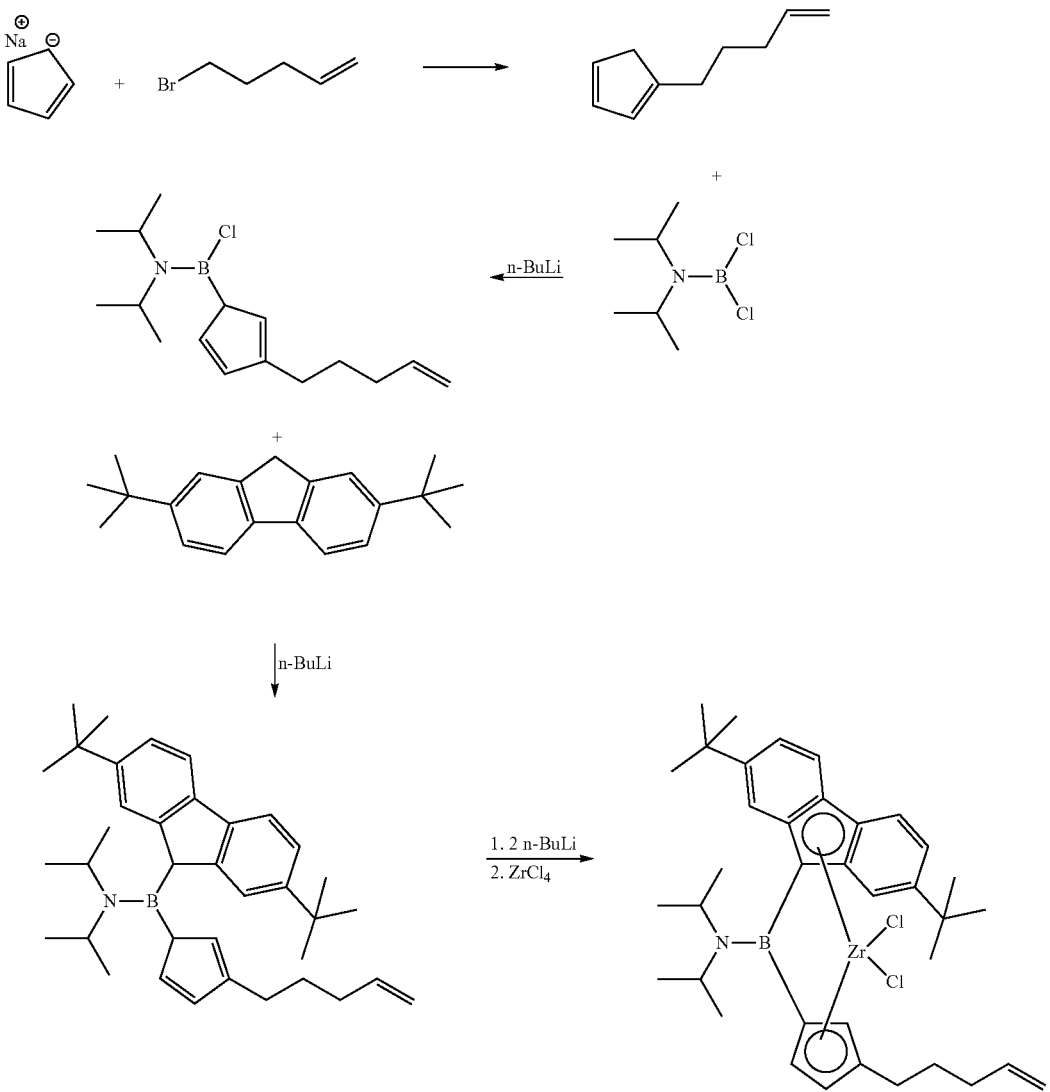

Also encompassed herein are ligand compounds which can be used to form metallocene compounds having formula (I). Such ligand compounds can have the formula:

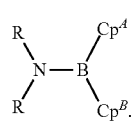

(A)

The selections for $Cp^A$, $Cp^B$, and each R in formula (A) are the same as those described herein above for formula (I).

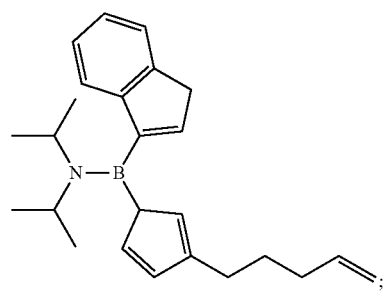

-continued

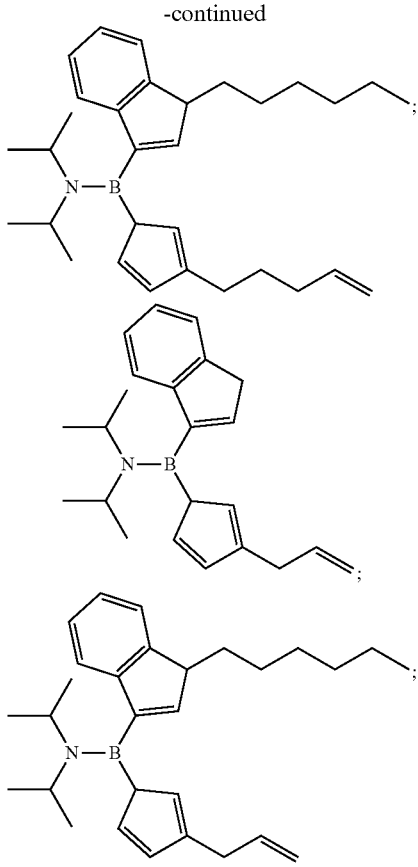

and the like.

Illustrative and non-limiting examples of cyclopentadienyl-fluorenyl boron-bridged ligand compounds (with the alkenyl substituent on the cyclopentadienyl group) can include the following compounds:

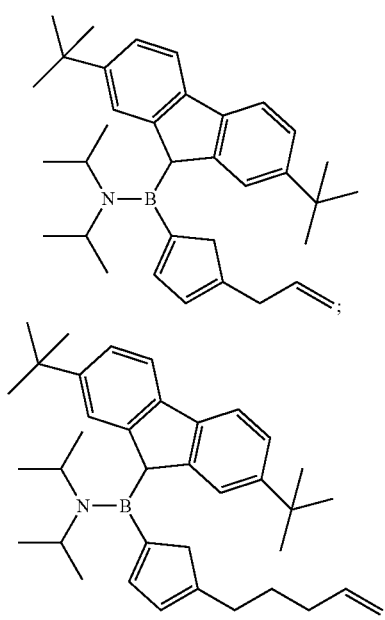

and the like.

Illustrative and non-limiting examples of indenyl-indenyl boron-bridged ligand compounds (with the alkenyl substituent on an indenyl group) can include the following compounds:

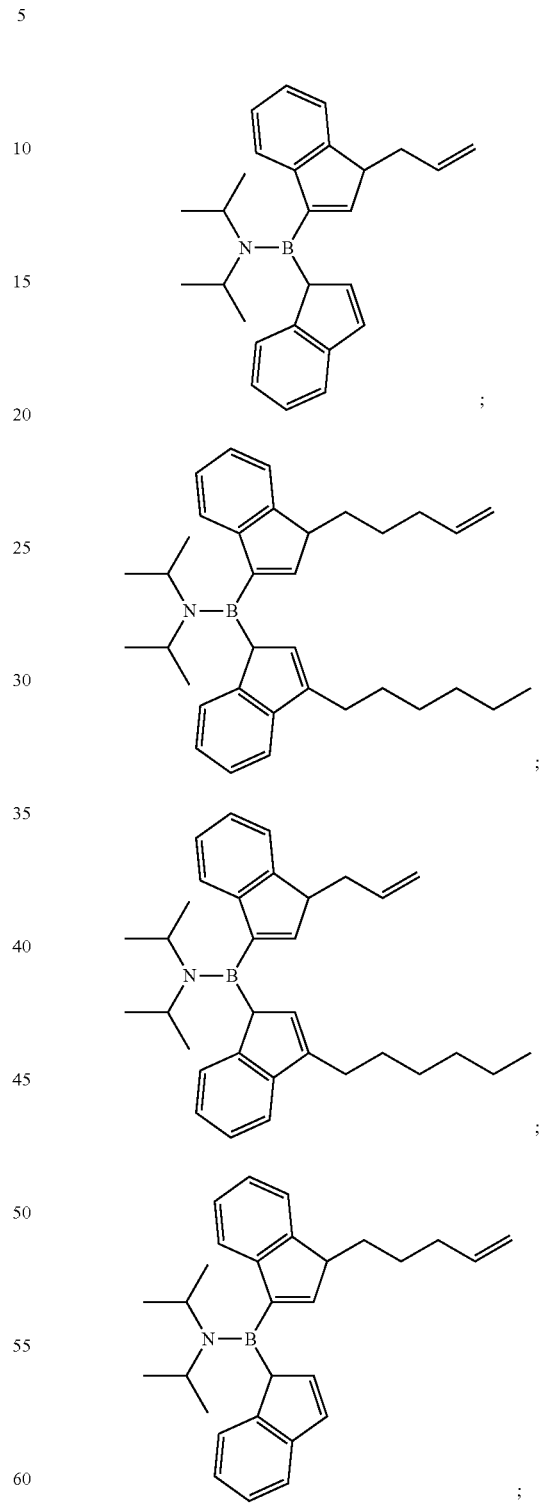

and the like.

Illustrative and non-limiting examples of cyclopentadienyl-indenyl boron-bridged ligand compounds (with the alkenyl substituent on the indenyl group) can include the following compounds:

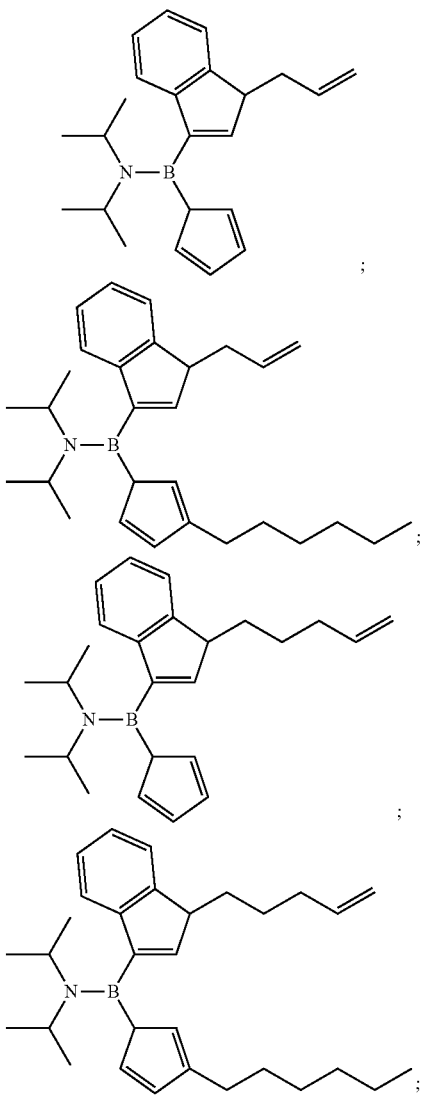

and the like.

Using analogous synthesis schemes to those provided herein, ligand and metallocene complexes with substituents on the nitrogen other than isopropyl can be derived, and complexes with cyclopentadienyl and fluorenyl groups with various alkenyl substituents (and optionally, other substituents) can be derived. Moreover, using analogous synthesis schemes to those provided herein, metallocene complexes with monoanionic ligands other than Cl (e.g., hydrocarbyl, hydrocarbylaminyl, hydrocarbylsilyl, etc.) can be derived, and complexes with various transition metals can be derived.

Activator-Supports

The present invention encompasses various catalyst compositions containing an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, and 8,309,485, 8,623, 973, and 8,703,886, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also can encompass oxide materials such as silica-coated alumina, as described in U.S. Pat. No. 7,884,163.

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one aspect, the silica content of these solid oxides can be from about 10 to about 80%, or from about 20% to about 70%, silica by weight. In another aspect, such materials can have silica contents ranging from about 15% to about 60%, or from about 25% to about 50%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 to about 25 wt. % of the electron-withdrawing anion, based on the weight of the activator-support. In particular aspects provided herein, the activator-support can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, or from about 4 to about 10 wt. %, of the electron-withdrawing anion, based on the total weight of the activator-support.

In an aspect, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, as well as any mixture or combination thereof. In another aspect, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. In yet another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; or alternatively, fluorided silica-coated alumina.

Various processes can be used to form activator-supports useful in the present invention. Methods of contacting the solid oxide with the electron-withdrawing component, suitable electron withdrawing components and addition amounts, impregnation with metals or metals ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, etc.) are well known to those of skill in the art.

Co-Catalysts

In certain aspects directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound, an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Representative and non-limiting examples of organoboron/organoborate compounds include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl)ammonium tetrakis(p-tolyl)borate, tri(n-butyl)ammonium tetrakis (m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(t-rimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms, or from 3 to 10 carbon atoms, in their molecular chain.

Acyclic, cyclic, polycyclic, terminal (a), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene can also be employed as a monomer in the present invention. In an aspect, the olefin monomer can comprise a $C_2$-$C_{20}$ olefin; alternatively, a $C_2$-$C_{20}$ alpha-olefin; alternatively, a $C_2$-$C_{10}$ olefin; alternatively, a $C_2$-$C_{10}$ alpha-olefin; alternatively, the olefin monomer can comprise ethylene; or alternatively, the olefin monomer can comprise propylene.

When a copolymer (or alternatively, a terpolymer) is desired, the olefin monomer and the olefin comonomer independently can comprise, for example, a $C_2$-$C_{20}$ alpha-olefin. In some aspects, the olefin monomer can comprise ethylene or propylene, which is copolymerized with at least one comonomer (e.g., a $C_2$-$C_{20}$ alpha-olefin, a $C_3$-$C_{20}$ alpha-olefin, etc.). According to one aspect of this invention, the olefin monomer used in the polymerization process can comprise ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect of the present invention, the olefin monomer can comprise ethylene, and the comonomer can comprise a $C_3$-$C_{10}$ alpha-olefin; alternatively, the comonomer can comprise 1-butene, 1-pentene, 1-hexene, 1-octene, 1-decene, styrene, or any combination thereof; alternatively, the comonomer can comprise 1-butene, 1-hexene, 1-octene, or any combination thereof; alternatively, the comonomer can comprise 1-butene; alternatively, the comonomer can comprise 1-hexene; or alternatively, the comonomer can comprise 1-octene.

Generally, the amount of comonomer introduced into a polymerization reactor system to produce a copolymer can be from about 0.01 to about 50 weight percent of the comonomer based on the total weight of the monomer and comonomer. According to another aspect of the present invention, the amount of comonomer introduced into a polymerization reactor system can be from about 0.01 to about 40 weight percent comonomer based on the total weight of the monomer and comonomer. In still another aspect, the amount of comonomer introduced into a polymerization reactor system can be from about 0.1 to about 35 weight percent comonomer based on the total weight of the monomer and comonomer. Yet, in another aspect, the amount of comonomer introduced into a polymerization reactor system can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one aspect of the present invention, at least one monomer/reactant can be ethylene (or propylene), so the polymerization reaction can be a homopolymerization involving only ethylene (or propylene), or a copolymerization with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

In some aspects, the present invention employs catalyst compositions containing a boron-bridged, cyclopentadienyl-fluorenyl metallocene compound and an activator (one or more than one). These catalyst compositions can be utilized to produce polyolefins—homopolymers, copolymers, and the like—for a variety of end-use applications. Boron-bridged metallocene compounds are discussed hereinabove. In aspects of the present invention, it is contemplated that the catalyst composition can contain more than one boron-bridged metallocene compound. Further, additional catalytic compounds—other than those specified as a boron-bridged metallocene compound—can be employed in the catalyst compositions and/or the polymerization processes, provided that the additional catalytic compound does not detract from the advantages disclosed herein. Additionally, more than one activator also may be utilized.

Generally, catalyst compositions of the present invention comprise a boron-bridged metallocene compound having formula (I) and an activator. In aspects of the invention, the activator can comprise an activator-support (e.g., an activator-support comprising a solid oxide treated with an electron-withdrawing anion). Activator-supports useful in the present invention are disclosed above. Optionally, such catalyst compositions can further comprise one or more than one co-catalyst compound or compounds (suitable co-catalysts, such as organoaluminum compounds, also are discussed above). Thus, a catalyst composition of this invention can comprise a boron-bridged metallocene compound, an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof; or alternatively, a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with aspects of the invention can comprise (or consist essentially of, or consist of) a boron-bridged metallocene compound; sulfated alumina (or fluorided silica-alumina, or fluorided silica-coated alumina); and triethylaluminum (or triisobutylaluminum).

In another aspect of the present invention, a catalyst composition is provided which comprises a boron-bridged metallocene compound, an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, discussed below, in the absence of these additional materials. For example, a catalyst composition of the present invention can consist essentially a boron-bridged metallocene compound, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a boron-bridged metallocene compound and an activator-support can further comprise an optional co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof; or alternatively, organoaluminum compounds, organozinc compounds, organomagnesium compounds, organolithium compounds, or any combination thereof. More than one co-catalyst can be present in the catalyst composition.

In a different aspect, a catalyst composition is provided which does not require an activator-support. Such a catalyst composition can comprise a boron-bridged metallocene compound and an activator, wherein the activator can comprise an aluminoxane compound, an organoboron or organoborate compound, an ionizing ionic compound, or combinations thereof; alternatively, an aluminoxane compound; alternatively, an organoboron or organoborate compound; or alternatively, an ionizing ionic compound.

In a particular aspect contemplated herein, the catalyst composition is a catalyst composition comprising an activator (one or more than one) and only one boron-bridged metallocene compound having formula (I). In these and other aspects, the catalyst composition can comprise an activator (e.g., an activator-support comprising a solid oxide treated with an electron-withdrawing anion), only one boron-bridged metallocene compound, and a co-catalyst (one or more than one), such as an organoaluminum compound.

This invention further encompasses methods of making these catalyst compositions, such as, for example, contacting the respective catalyst components in any order or sequence. In one aspect, the catalyst composition can be produced by a process comprising contacting the metallocene compound and the activator, while in another aspect, the catalyst composition can be produced by a process comprising contacting, in any order, the metallocene compound, the activator, and the co-catalyst.

Generally, the weight ratio of organoaluminum compound to activator-support can be in a range from about 10:1 to about 1:1000. If more than one organoaluminum compound and/or more than one activator-support are employed, this ratio is based on the total weight of each respective component. In another aspect, the weight ratio of the organoaluminum compound to the activator-support can be in a range from about 3:1 to about 1:100, or from about 1:1 to about 1:50.

In some aspects of this invention, the weight ratio of metallocene compound to activator-support can be in a range from about 1:1 to about 1:1,000,000. If more than one metallocene compound and/or more than activator-support is/are employed, this ratio is based on the total weights of the respective components. In another aspect, this weight ratio can be in a range from about 1:5 to about 1:100,000, or from about 1:10 to about 1:10,000. Yet, in another aspect, the weight ratio of the metallocene compound to the activator-support can be in a range from about 1:20 to about 1:1000.

Catalyst compositions of the present invention generally have a catalyst activity greater than about 100,000 grams of ethylene polymer (homopolymer or copolymer, as the context requires) per gram of the boron-bridged metallocene compound per hour (abbreviated g/g/h). In another aspect, the catalyst activity can be greater than about 200,000, greater than about 250,000, or greater than about 500,000 g/g/h. In still another aspect, catalyst compositions of this invention can be characterized by having a homopolymer catalyst activity (or copolymer catalyst activity) greater than about 1,000,000, greater than about 1,500,000, or greater than about 2,000,000 g/g/h, and often can range up to 3,000,000-4,000,000 g/g/h. These activities are measured under slurry polymerization conditions, with a triisobutylaluminum co-catalyst, using isobutane as the diluent, at a polymerization temperature of 80° C. and a reactor pressure of about 390 psig. Additionally, in some aspects, the activator can comprise an activator-support, such as sulfated alumina, fluorided silica-alumina, or fluorided silica-coated alumina, although not limited thereto.

Polymerization Processes

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) in a polymerization reactor system under polymerization conditions to produce an olefin polymer, wherein the catalyst composition can comprise a boron-bridged metallocene compound, an activator, and an optional co-catalyst. Suitable boron-bridged metallocene compounds, activators, and co-catalysts are discussed herein.

In accordance with one aspect of the invention, the polymerization process can employ a catalyst composition comprising a boron-bridged metallocene compound having formula (I) and an activator, wherein the activator comprises an activator-support. The catalyst composition, optionally, can further comprise one or more than one organoaluminum compound or compounds (or other suitable co-catalyst). Thus, a process for polymerizing olefins in the presence of a catalyst composition can employ a catalyst composition comprising a boron-bridged metallocene compound, an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof; or alternatively, a fluorided solid oxide and/or a sulfated solid oxide. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a boron-bridged metallocene, an activator-support, and an optional co-catalyst, wherein the co-catalyst can comprise an aluminoxane compound, an organoboron or organoborate compound, an ionizing ionic compound, an organoaluminum compound, an organozinc compound, an organomagnesium compound, or an organolithium compound, or any combination thereof. Hence, aspects of this invention are directed to a process for polymerizing olefins in the presence of a catalyst composition, the processes comprising contacting a catalyst composition with an olefin monomer and optionally an olefin comonomer (one or more) under polymerization conditions to produce an olefin polymer, and the catalyst composition can comprise a boron-bridged metallocene compound, an activator-support, and an aluminoxane compound; alternatively, a boron-bridged metallocene compound, an activator-support, and an organoboron or organoborate compound; alternatively, a boron-bridged metallocene compound, an activator-support, and an ionizing ionic compound; alternatively, a boron-bridged metallocene compound, an activator-support, and an organoaluminum compound; alternatively, a boron-bridged metallocene compound, an activator-support, and an organozinc compound; alternatively, a boron-bridged metallocene compound, an activator-support, and an organomagnesium compound; or alternatively, a boron-bridged metallocene compound, an activator-support, and an organolithium compound. Furthermore, more than one co-catalyst can be employed, e.g., an organoaluminum compound and an aluminoxane compound, an organoaluminum compound and an ionizing ionic compound, etc.

In accordance with another aspect of the invention, the polymerization process can employ a catalyst composition comprising only one boron-bridged metallocene compound, an activator-support, and an organoaluminum compound.

In accordance with yet another aspect of the invention, the polymerization process can employ a catalyst composition comprising a boron-bridged metallocene compound and an activator, wherein the activator comprises an aluminoxane compound, an organoboron or organoborate compound, an ionizing ionic compound, or combinations thereof; alternatively, an aluminoxane compound; alternatively, an organoboron or organoborate compound; or alternatively, an ionizing ionic compound.

The catalyst compositions of the present invention are intended for any olefin polymerization method using various types of polymerization reactor systems and reactors. The polymerization reactor system can include any polymerization reactor capable of polymerizing olefin monomers and comonomers (one or more than one comonomer) to produce homopolymers, copolymers, terpolymers, and the like. The various types of reactors include those that can be referred to as a batch reactor, slurry reactor, gas-phase reactor, solution reactor, high pressure reactor, tubular reactor, autoclave reactor, and the like, or combinations thereof. Suitable polymerization conditions are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge. Processes can also include partial or full direct recycle of unreacted monomer, unreacted comonomer, and/or diluent.

Polymerization reactor systems of the present invention can comprise one type of reactor in a system or multiple reactors of the same or different type (e.g., a single reactor, dual reactor, more than two reactors). Production of polymers in multiple reactors can include several stages in at least two separate polymerization reactors interconnected by a transfer device making it possible to transfer the polymers resulting from the first polymerization reactor into the second reactor. The desired polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both. Accordingly, the present invention encompasses polymerization reactor systems comprising a single reactor, comprising two reactors, and comprising more than two reactors. The polymerization reactor system can comprise a slurry reactor, a gas-phase reactor, a solution reactor, in certain aspects of this invention, as well as multi-reactor combinations thereof.

According to one aspect of the invention, the polymerization reactor system can comprise at least one loop slurry reactor comprising vertical or horizontal loops. Monomer, diluent, catalyst, and comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under polymerization conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor system can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect of the invention, the polymerization reactor system can comprise a solution polymerization reactor wherein the monomer (and comonomer, if used) are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the present invention can further comprise any combination of at least one raw material feed system, at least one feed system for catalyst or catalyst components, and/or at least one polymer recovery system. Suitable reactor systems for the present invention can further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 60° C. to about 280° C., for example, or from about 60° C. to about 120° C., depending upon the type of polymerization reactor(s). In some reactor systems, the polymerization temperature generally can fall within a range from about 70° C. to about 100° C., or from about 75° C. to about 95° C. Various polymerization conditions can be held substantially constant, for example, for the production of a particular grade of olefin polymer.

Suitable pressures will also vary according to the reactor and polymerization type. The pressure for liquid phase polymerizations in a loop reactor is typically less than 1000 psig (6.9 MPa). Pressure for gas phase polymerization is usually at about 200 to 500 psig (1.4 MPa to 3.4 MPa). High pressure polymerization in tubular or autoclave reactors is generally run at about 20,000 to 75,000 psig (138 to 517 MPa). Polymerization reactors can also be operated in a supercritical region occurring at generally higher temperatures and pressures. Operation above the critical point of a pressure/temperature diagram (supercritical phase) may offer advantages.

Aspects of this invention are directed to olefin polymerization processes comprising contacting a catalyst composition with an olefin monomer and, optionally, an olefin comonomer under polymerization conditions to produce an olefin polymer. The olefin polymer (e.g., ethylene homopolymer, ethylene copolymer, etc.) produced by the process can have any of the polymer properties disclosed herein, for example, a density from about 0.91 to about 0.96 g/cm$^3$, and/or less than about 0.005 LCB per 1000 total carbon atoms, and/or a ratio of Mw/Mn from about 2 to about 8, and/or a ratio of Mz/Mw from about 1.5 to about 5, and/or a conventional or substantially flat comonomer distribution.

Aspects of this invention also are directed to olefin polymerization processes conducted in the absence of added hydrogen. An olefin polymerization process of this invention can comprise contacting a catalyst composition with an olefin monomer and optionally an olefin comonomer in a polymerization reactor system under polymerization conditions to produce an olefin polymer, wherein the catalyst composition can comprise a boron-bridged metallocene, an activator, and an optional co-catalyst, and wherein the polymerization process is conducted in the absence of added hydrogen (no hydrogen is added to the polymerization reactor system). As one of ordinary skill in the art would recognize, hydrogen can be generated in-situ by metallocene catalyst compositions in various olefin polymerization processes, and the amount generated can vary depending upon the specific catalyst composition and metallocene compound employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer in a polymerization reactor system under polymerization conditions to produce an olefin polymer, wherein the catalyst composition comprises a boron-bridged metallocene, an activator, and an optional co-catalyst, and wherein the polymerization process is conducted in the presence of added hydrogen (hydrogen is added to the polymerization reactor system). For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In a particular aspect and unexpectedly, the Mw/Mn ratio of the olefin polymer produced by the process can increase as the amount of hydrogen added to the polymerization reactor system increases. For instance, the Mw/Mn ratio of the polymer produced by the process in absence of added hydrogen (zero added hydrogen, molar ratio of $H_2$:olefin monomer equal to zero) can be less than the Mw/Mn of a polymer produced by the process in the presence of hydrogen at a molar ratio of $H_2$:olefin monomer of 0.1:1, under the same polymerization conditions. In another aspect, the Mw/Mn ratio of the polymer produced by the process in the presence of hydrogen at a molar ratio of $H_2$:olefin monomer equal to 0.1:1 can be less than the Mw/Mn of a polymer produced by the process in the presence of hydrogen at a molar ratio of $H_2$:olefin monomer of 0.25:1, under the same polymerization conditions. The same polymerization conditions means that all components used to prepare the catalyst systems are held constant (e.g., same amount/type of metallocene compound, same amount/type of co-catalyst, same amount/type of activator, such as fluorided silica-coated alumina, etc.) and all polymerization conditions are held constant (e.g., same polymerization temperature, same pressure, etc.). Hence, the only difference is the amount of hydrogen present during the polymerization.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S.

Patent Publication No. 2004/0059070, the disclosures of which are incorporated herein by reference in their entirety.

The concentration of the reactants entering the polymerization reactor system can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers produced by any of the polymerization processes disclosed herein. Articles of manufacture can be formed from, and/or can comprise, the polymers produced in accordance with this invention.

Polymers and Articles

Olefin polymers encompassed herein can include any polymer produced from any olefin monomer and optional comonomer(s) described herein. For example, the olefin polymer can comprise an ethylene homopolymer, an ethylene copolymer (e.g., ethylene/α-olefin, ethylene/1-butene, ethylene/1-hexene, ethylene/1-octene, etc.), a propylene homopolymer, a propylene copolymer, an ethylene terpolymer, a propylene terpolymer, and the like, including combinations thereof. In one aspect, the olefin polymer can be an ethylene/1-butene copolymer, an ethylene/1-hexene copolymer, or an ethylene/1-octene copolymer, while in another aspect, the olefin polymer can be an ethylene/1-hexene copolymer.

If the resultant polymer produced in accordance with the present invention is, for example, an ethylene polymer, its properties can be characterized by various analytical techniques known and used in the polyolefin industry. Articles of manufacture can be formed from, and/or can comprise, the olefin polymers (e.g., ethylene polymers) of this invention, whose typical properties are provided below.

The densities of ethylene-based polymers produced using the catalyst systems and processes disclosed herein often are greater than or equal to about 0.89 g/cm$^3$. In one aspect of this invention, the density of the ethylene polymer can be in a range from about 0.89 to about 0.96 g/cm$^3$. Yet, in another aspect, the density can be in a range from about 0.90 to about 0.96 g/cm$^3$, such as, for example, from about 0.91 to about 0.96 g/cm$^3$, from about 0.92 to about 0.95 g/cm$^3$, or from about 0.91 to about 0.94 g/cm$^3$.

Ethylene polymers, such as homopolymers, copolymers, etc., consistent with various aspects of the present invention generally have a ratio of Mw/Mn, or the polydispersity index, in a range from about 2 to about 12. In some aspects disclosed herein, the ratio of Mw/Mn can be in a range from about 2 to about 8, from about 2 to about 6, or from about 2.5 to about 5.5. In other aspects, the ratio of Mw/Mn can be in a range from about 2 to about 5, from about 2 to about 4, from about 2.2 to about 6, from about 2.2 to about 5, or from about 2.2 to about 3.8. Additionally or alternatively, the ratio of Mz/Mw of the polymer can be in a range from about 1.5 to about 5, from about 1.5 to about 4, from about 1.5 to about 3, from about 1.7 to about 4.5, from about 1.8 to about 4, or from about 1.8 to about 2.8.

Generally, polymers produced in aspects of the present invention have low levels of long chain branching, with typically less than about 0.01 long chain branches (LCB) per 1000 total carbon atoms, and more often, less than about 0.008 LCB per 1000 total carbon atoms. In some aspects, the number of LCB per 1000 total carbon atoms can be less than about 0.005, or less than about 0.003 LCB per 1000 total carbon atoms. Further, the olefin polymer can have less than about 0.002 LCB per 1000 total carbon atoms in particular aspects of this invention.

Ethylene copolymers, for example, produced using the polymerization processes and catalyst systems described hereinabove can, in some aspects, have a conventional comonomer distribution, generally, the lower molecular weight components of the polymer have higher comonomer incorporation than the higher molecular weight components. Typically, there is decreasing comonomer incorporation with increasing molecular weight. In one aspect, the number of short chain branches (SCB) per 1000 total carbon atoms of the polymer can be greater at Mn than at Mw. In another aspect, the number of SCB per 1000 total carbon atoms of the polymer can be greater at Mn than at Mz.

Yet, in other aspects, ethylene copolymers produced using the polymerization processes and catalyst systems described hereinabove can have a substantially flat comonomer distribution. For instance, the number of SCB per 1000 total carbon atoms of the polymer at Mn can be within +/−10-15% of the number of SCB per 1000 total carbon atoms at Mw. Additionally or alternatively, the number of SCB per 1000 total carbon atoms of the polymer at Mw can be within +/−10-15% of the number of SCB per 1000 total carbon atoms at Mz.

Polymers of ethylene, whether homopolymers, copolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Applicants also contemplate a method for forming or preparing an article of manufacture comprising a polymer produced by any of the polymerization processes disclosed herein. For instance, a method can comprise (i) contacting a catalyst composition with an olefin monomer and an optional olefin comonomer under polymerization conditions in a polymerization reactor system to produce an olefin polymer, wherein the catalyst composition can comprise a boron-bridged metallocene, an activator (e.g., an activator-support comprising a solid oxide treated with an electron-withdrawing anion), and an optional co-catalyst (e.g., an organoaluminum compound); and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Melt index (MI, g/10 min) was determined in accordance with ASTM D1238 at 190° C. with a 2,160 gram weight. High load melt index (HLMI, g/10 min) was determined in accordance with ASTM D1238 at 190° C. with a 21,600 gram weight.

Polymer density was determined in grams per cubic centimeter (g/cm$^3$) on a compression molded sample, cooled at about 15° C. per hour, and conditioned for about 40 hours at room temperature in accordance with ASTM D1505 and ASTM D4703.

Molecular weights and molecular weight distributions were obtained using a PL-GPC 220 (Polymer Labs, an Agilent Company) system equipped with a IR4 detector (Polymer Char, Spain) and three Styragel HMW-6E GPC columns (Waters, Mass.) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation was conducted at 150° C. for nominally 4 hr with occasional and gentle agitation, before the solutions were transferred to sample vials for injection. An injection volume of about 200 µL was used. The integral calibration method was used to deduce molecular weights and molecular weight distributions using a Chevron Phillips Chemicals Company's HDPE polyethylene resin, MARLEX® BHB5003, as the broad standard. The integral table of the broad standard was pre-determined in a separate experiment with SEC-MALS. Mn is the number-average molecular weight, Mw is the weight-average molecular weight, and Mz is the z-average molecular weight.

Melt rheological characterizations were performed as follows. Small-strain (10%) oscillatory shear measurements were performed on a Rheometrics Scientific, Inc. ARES rheometer using parallel-plate geometry. All rheological tests were performed at 190° C. The complex viscosity |η*| versus frequency (ω) data were then curve fitted using the modified three parameter Carreau-Yasuda (CY) empirical model to obtain the zero shear viscosity—$\eta_0$, characteristic viscous relaxation time—$\tau_\eta$, and the breadth parameter—a. The simplified Carreau-Yasuda (CY) empirical model is as follows.

$$|\eta*(\omega)| = \frac{\eta_0}{[1+(\tau_\eta \omega)^a]^{(1-n)/a}},$$

wherein: |η*(ω)|=magnitude of complex shear viscosity;
$\eta_0$=zero shear viscosity;
$\tau_\eta$=viscous relaxation time (Tau(η));
a="breadth" parameter (CY-a parameter);
n=fixes the final power law slope, fixed at 2/11; and
ω=angular frequency of oscillatory shearing deformation.

Details of the significance and interpretation of the CY model and derived parameters may be found in: C. A. Hieber and H. H. Chiang, *Rheol. Acta*, 28, 321 (1989); C. A. Hieber and H. H. Chiang, *Polym. Eng. Sci.*, 32, 931 (1992); and R. B. Bird, R. C. Armstrong and O. Hasseger, *Dynamics of Polymeric Liquids, Volume 1, Fluid Mechanics*, 2nd Edition, John Wiley & Sons (1987); each of which is incorporated herein by reference in its entirety.

The long chain branches (LCB) per 1000 total carbon atoms were calculated using the method of Janzen and Colby (*J. Mol. Struct.*, 485/486, 569-584 (1999)), from values of zero shear viscosity, $\eta_o$ (determined from the Carreau-Yasuda model), and measured values of Mw obtained using a Dawn EOS multiangle light scattering detector (Wyatt). See also U.S. Pat. No. 8,114,946; J. Phys. Chem. 1980, 84, 649; and Y. Yu, D.C. Rohlfing, G. R Hawley, and P. J. DesLauriers, *Polymer Preprint*, 44, 50, (2003). These references are incorporated herein by reference in their entirety.

Short chain branch (SCB) content and short chain branching distribution (SCBD) across the molecular weight distribution were determined via an IR5-detected GPC system (IR5-GPC), wherein the GPC system was a PL220 GPC/SEC system (Polymer Labs, an Agilent company) equipped with three Styragel HMW-6E columns (Waters, Mass.) for polymer separation. A thermoelectric-cooled IR5 MCT detector (IR5) (Polymer Char, Spain) was connected to the GPC columns via a hot-transfer line. Chromatographic data were obtained from two output ports of the IR5 detector. First, the analog signal goes from the analog output port to a digitizer before connecting to Computer "A" for molecular weight determinations via the Cirrus software (Polymer Labs, now an Agilent Company) and the integral calibration method using a broad MWD HDPE Marlex™ BHB5003 resin (Chevron Phillips Chemical) as the broad molecular weight standard. The digital signals, on the other hand, go via a USB cable directly to Computer "B" where they are collected by a LabView data collection software provided by Polymer Char. Chromatographic conditions were set as follows: column oven temperature of 145° C.; flowrate of 1 mL/min; injection volume of 0.4 mL; and polymer concentration of about 2 mg/mL, depending on sample molecular weight. The temperatures for both the hot-transfer line and IR5 detector sample cell were set at 150° C., while the temperature of the electronics of the IR5 detector was set at 60° C. Short chain branching content was determined via an in-house method using the intensity ratio of CH$_3$ ($I_{CH3}$) to CH$_2$ ($I_{CH2}$) coupled with a calibration curve. The calibration curve was a plot of SCB content ($x_{SCB}$) as a function of the intensity ratio of $I_{CH3}/I_{CH2}$. To obtain a calibration curve, a group of polyethylene resins (no less than 5) of SCB level ranging from zero to ca. 32 SCB/1,000 total carbons (SCB Standards) were used. All these SCB Standards have known SCB levels and flat SCBD profiles pre-determined separately by NMR and the solvent-gradient fractionation coupled with NMR (SGF-NMR) methods. Using SCB calibration curves thus established, profiles of short chain branching distribution across the molecular weight distribution were obtained for resins fractionated by the IR5-GPC system under exactly the same chromatographic conditions as for these SCB standards. A relationship between the intensity ratio and the elution volume was converted into SCB distribution as a function of MWD using a predetermined SCB calibration curve (i.e., intensity ratio of $I_{CH3}/I_{CH2}$ vs. SCB content) and MW calibration curve (i.e., molecular weight vs. elution time) to convert the intensity ratio of $I_{CH3}/I_{CH2}$ and the elution time into SCB content and the molecular weight, respectively.

Fluorided silica-coated aluminas were prepared as follows. Alumina A, from W.R. Grace Company, was impregnated to incipient wetness was first calcined in dry air at about 600° C. for approximately 6 hours, cooled to ambient temperature, and then contacted with tetraethylorthosilicate in isopropanol to equal 25 wt. % SiO$_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. (unless otherwise noted) in dry air. Afterward, the fluorided silica-coated alumina was collected and stored under dry nitrogen, and was used without exposure to the atmosphere.

Example 1

In Example 1, metallocene MET-A, shown below, was synthesized by first reacting sodium cyclopentadiene with 5-bromo-1-pentene, to form a pentenyl substituted cyclopentadiene, which was isolated in good yield. One mole of this compound was lithiated and reacted with one mole of dichloro(diisopropylamino) borane in diethyl ether at −78° C. The resulting solution was warmed to 20° C. for 12 hr, then cooled down again to −78° C., and then a diethyl ether solution of lithiated 2,7-di-tert-butylfluorine was added. The resulting orange slurry was stirred for 12 hr while warming to 20° C. The solvent was removed under reduced pressure, and the resulting dark red/orange oil was removed in 10 mL of pentane (this solution was then placed in a freezer at −34° C. for 12 hr). The ligand shown below was isolated as an orange solid:

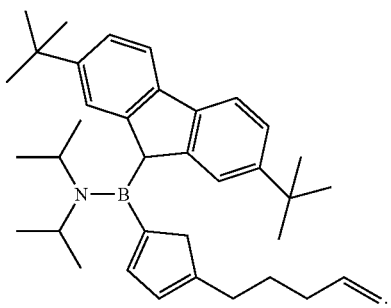 [SMILES: C=CCCCC1=CC=C(B(C2c3cc(C(C)(C)C)ccc3-c3ccc(C(C)(C)C)cc32)N(C(C)C)C(C)C)C1]

A portion of the ligand product was mixed with diethyl ether and cooled to −34° C., and then mixed with a diethyl ether solution of lithium diisopropylamine, resulting in a bright orange slurry, followed by warming to 20° C. while stirring. A suspension of $ZrCl_4$ in diethyl ether was cooled to −34° C., following by addition of the ligand mixture. After first turning dark orange, the resultant slurry then turned to bright orange. After stirring for 12 hr and warming to 20° C., the solvent was removed under reduced pressure, and the resultant orange solid was extracted with methylene chloride. After filtering to isolate the solid, the remaining solvent was removed at reduced pressure, resulting in MET-A as a bright orange solid {$^1$H NMR (300 MHz $C_6D_6$): δ 7.567-8.00 (4H, m), 7.024 (2H, m), 6.24 (1H, t), 5.58-5.779 (1H, m), 5.304 (1H, t), 4.825-5.137 (3H, m), 2.533 (2H, s), 0.737-1.782 (36H, m)}:

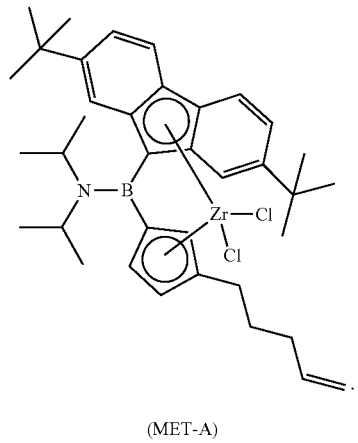

(MET-A)

Example 2

Using a synthesis procedure analogous to that of Example 1, the following ligand compound and metallocene compound (MET-B) were produced {mixture of rac/meso isomers—$^1$H NMR (300 MHz, $C_6D_6$): δ 7.26-7.34 (2H, m), 7.12-7.20 (2H, m), 6.94-7.03 (2H, m), 6.69-6.77 (2H, m), 5.69-5.80 (2H, m), 5.405 (1H, d), 5.22 (1H, s), 5.01 (1H, d), 4.97 (1H, d), 3.758-3.935 (2.76H, m), 2.95-3.08 (2.35H, m), 2.80-2.94 (2.55H, m), 2.02 (3.40H, m), 1.55-1.71 (3.77H, m), 1.07-1.26 (13.54H, m)}:

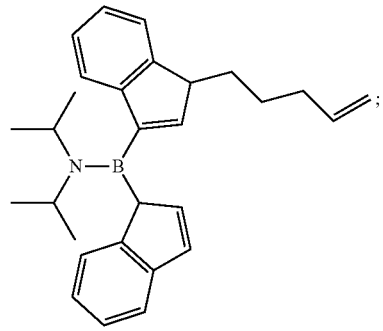

(Ligand-B)

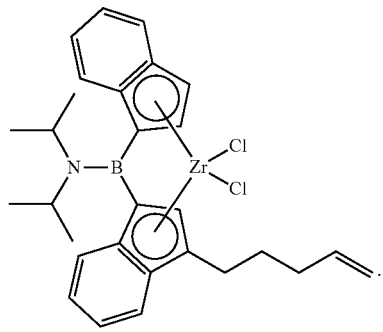

(MET-B)

Examples 3-5

Using a synthesis procedure analogous to that of Example 1, the following ligand compounds were produced:

(Example 3)

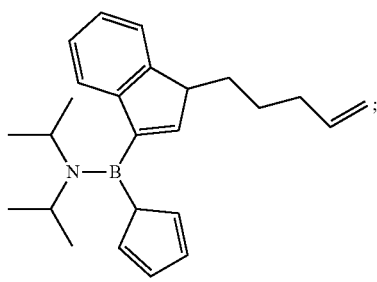

(Example 4)

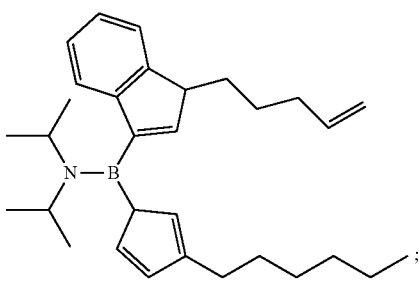

-continued (Example 5)

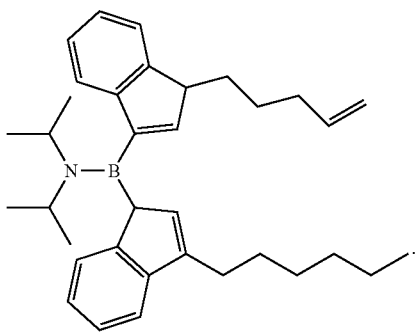

Examples 6-9

Examples 6-9 were produced using the following polymerization procedure. All polymerization runs were conducted in a one-gallon stainless steel reactor. Isobutane (1.2 L) was used in all runs. A metallocene solution of MET-A was prepared at about 1 mg/mL in toluene. Approximately 100 mg of fluorided silica-coated alumina, 0.5 mmol of alkyl aluminum (triisobutylaluminum), and the metallocene solution (containing 2 mg of MET-A) were added in that order through a charge port while slowly venting isobutane vapor. The charge port was closed and isobutane was added. The contents of the reactor were stirred and heated to the desired run temperature of about 80° C., and ethylene was then introduced into the reactor with 10 g (Example 6), 20 g (Example 7), 30 g (Example 8), or 40 g (Example 9) of 1-hexene. Ethylene was fed on demand to maintain the target pressure of 390 psig pressure for the length of the polymerization run, which was varied to produce substantially the same amount of polymer (about 150 g). The reactor was maintained at the desired run temperature throughout the run by an automated heating-cooling system. The catalyst activity for Examples 6-9 ranged from 200,000 to 600,000 grams of polymer per gram of MET-A per hour.

Figure 3:
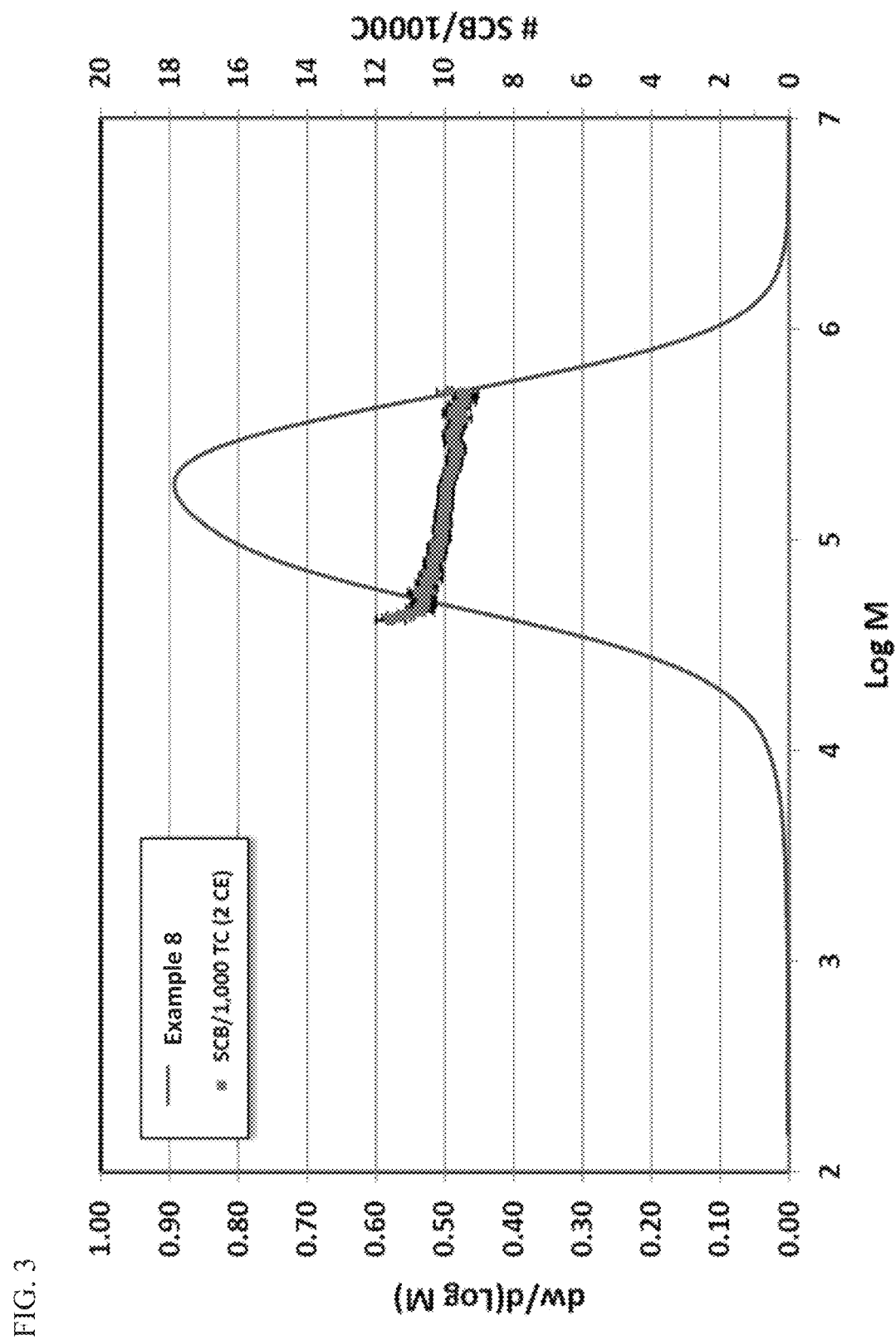
FIG. 3 presents a plot of the molecular weight distribution and short chain branch distribution of the polymer of Example 8.
Figure 4:
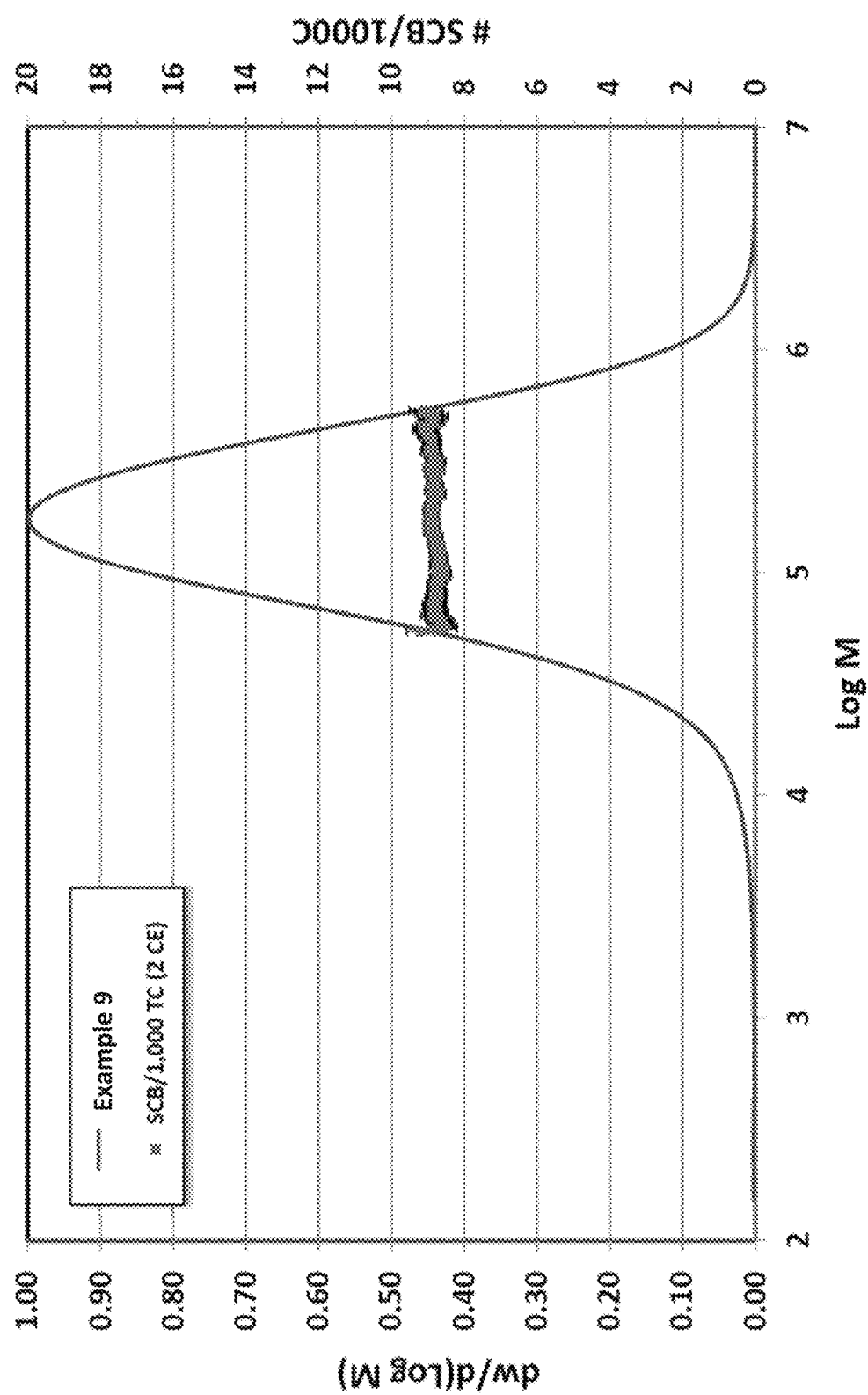
FIG. 4 presents a plot of the molecular weight distribution and short chain branch distribution of the polymer of Example 9.

FIGS. 1-4 illustrate the molecular weight distributions and short chain branch distributions of the polymers of Examples 6-9, respectively, while Table I summarizes various molecular weight and other polymer property characteristics for the polymers of Examples 6-9. In addition to relatively high molecular weights and narrow molecular weight distributions, the polymers of Examples 6-7 and 9 had a substantially flat comonomer distribution, while the polymer of Example 8 exhibited a conventional (decreasing) comonomer distribution (e.g., there are relatively more short chain branches (SCB) at the lower molecular weights; assumes 2 methyl chain ends (CE)). In FIG. 3, the number of SCB per 1000 total carbon (TC) atoms of the polymer at Mz (or Mw) is less than at Mn.

TABLE I

Polymer Properties of Examples 6-9.

| Example | 6 | 7 | 8 | 9 |
|---|---|---|---|---|
| MI (g/10 min) | 0 | 0 | 0 | 0 |
| HLMI (g/10 min) | 0.06 | 0.14 | 0.27 | 0.34 |
| Density (g/cm³) | 0.920 | 0.939 | 0.930 | 0.915 |
| Mn (kg/mol) | 142 | 101 | 125 | 127 |
| Mw (kg/mol) | 365 | 329 | 304 | 307 |

TABLE I-continued

Polymer Properties of Examples 6-9.

| Example | 6 | 7 | 8 | 9 |
|---|---|---|---|---|
| Mz (kg/mol) | 690 | 617 | 552 | 542 |
| Mw/Mn | 2.57 | 3.26 | 2.43 | 2.41 |
| Mz/Mw | 1.89 | 1.88 | 1.81 | 1.77 |

Example 10

Figure 5:
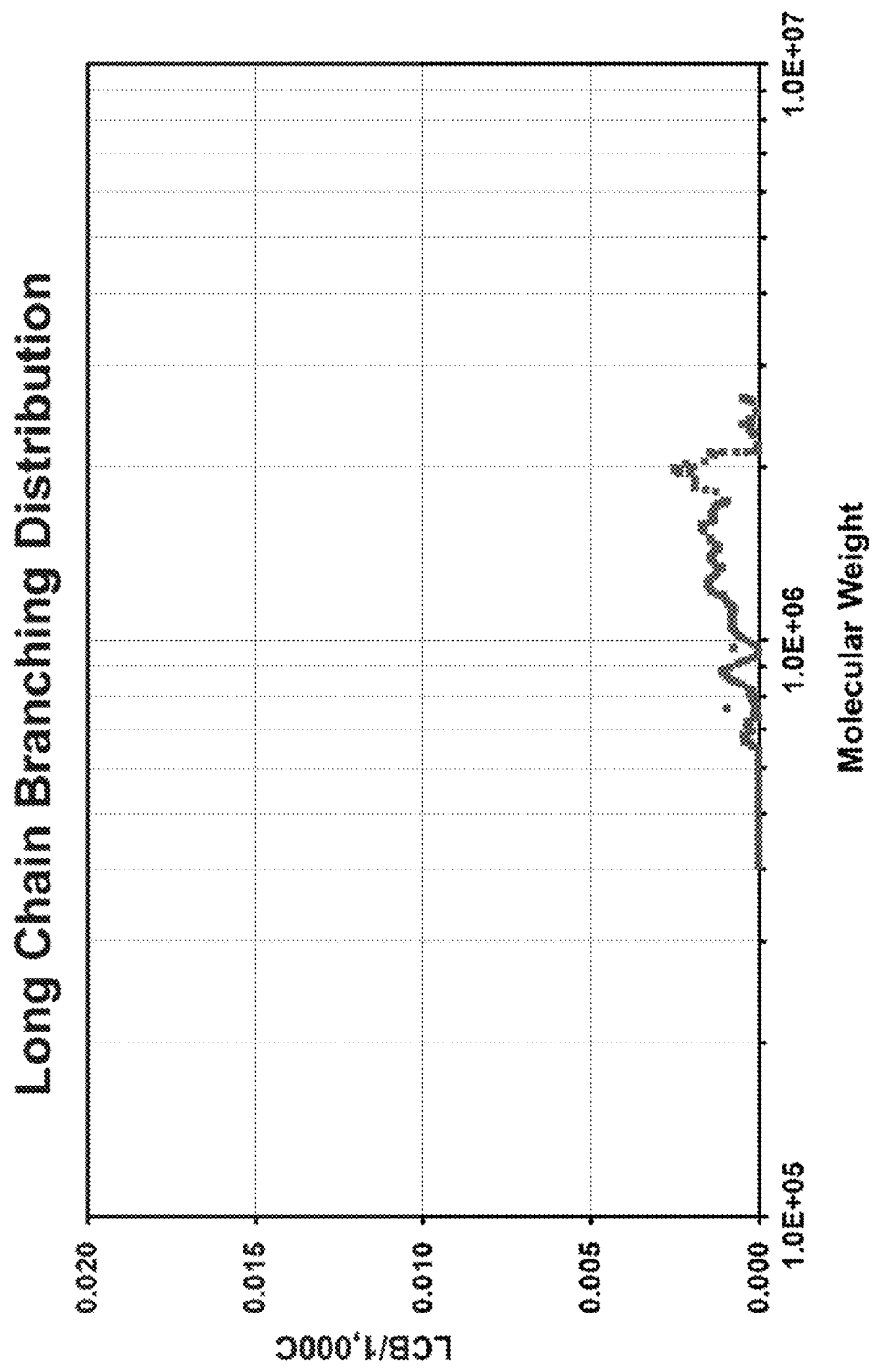
FIG. 5 presents a plot of the amount of long chain branches (LCB) per 1000 total carbon atoms as a function of the molecular weight of the polymer of Example 10.

Example 10 was performed in substantially the same manner as Examples 6-9 using MET-A, with the exception that no comonomer was used (i.e., an ethylene homopolymer was produced). Table II summarizes certain properties of the homopolymer of Example 10. The catalyst activity was about 500,000 grams of polymer per gram of MET-A per hour. As shown in Table II, the homopolymer of Example 10 had a high molecular weight, narrow molecular weight distribution, and a relatively low density for an ethylene homopolymer. The homopolymer of Example 10 also had very low levels of long chain branches (LCB), i.e., less than 0.005 per 1000 total carbon atoms. FIG. 5 illustrates the very low amount of LCB of the homopolymer of Example 10 produced using MET-A as a function of the polymer molecular weight.

TABLE II

Homopolymer Properties of Example 10.

| Example | 10 |
|---|---|
| MI (g/10 min) | 0 |
| HLMI (g/10 min) | <0.1 |
| Density (g/cm³) | 0.924 |
| Mn (kg/mol) | 204 |
| Mw (kg/mol) | 479 |
| Mz (kg/mol) | 950 |
| Mw/Mn | 2.35 |
| Mz/Mw | 1.98 |
| LCB/1000 TC's | <0.005 |

Examples 11-13

Figure 6:
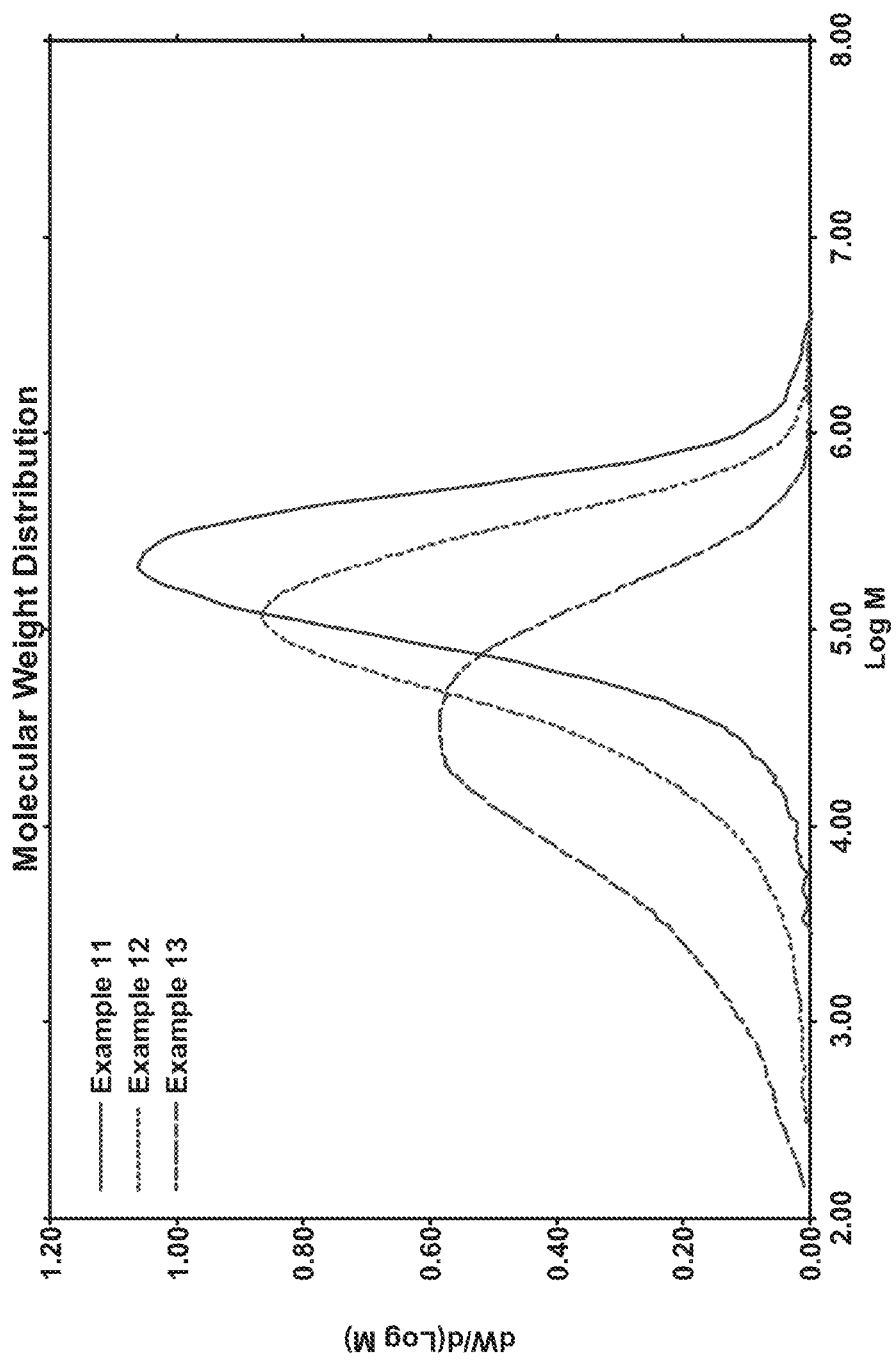
FIG. 6 presents a plot of the molecular weight distributions of the polymers of Examples 11-13, produced with different amounts of hydrogen present during polymerization.

Examples 11-13 were performed in substantially the same manner as Example 10, with the exception that certain amounts of hydrogen were added during polymerization (hydrogen was added with the ethylene feed at the specified percentage). FIG. 6 illustrates that the addition of hydrogen reduced the average polymer molecular weight (e.g., shifting curves to the left as hydrogen addition increased). Unexpectedly, however, the addition of hydrogen also broadened the molecular weight distribution (e.g., increased Mw/Mn), as summarized in Table III for the hydrogen:ethylene molar ratios used in Examples 11-13.

TABLE III

Hydrogen Impact on Molecular Weight Distribution.

| Example | 11 | 12 | 13 |
|---|---|---|---|
| H₂:ethylene | 0 | 0.1:1 | 0.25:1 |
| Mw/Mn | 2.3 | 6.0 | 11.0 |

Examples 14-16

Examples 14-16 were performed in substantially the same manner as Examples 6-9 using MET-A, with the exception that certain molar ratios of 1-hexene:ethylene were used during polymerization. As shown in Table IV, and unexpectedly, the catalyst system containing MET-A provided good comonomer incorporation, as illustrated by the relatively large drop in density based on the increase in the comonomer: monomer molar ratio.

TABLE IV

Comonomer 1-Hexene Impact on Density.

| Example | 14 | 15 | 16 |
|---|---|---|---|
| 1-hexene:ethylene | 0.034 | 0.068 | 0.140 |
| Density (g/cm³) | 0.9236 | 0.9176 | 0.9146 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A ligand compound having the formula:

$$\begin{array}{c}R\\ \diagdown\\ R\diagup\end{array} N-B\begin{array}{c}Cp^A\\ \diagdown\\ \diagup\\ Cp^B\end{array}\;; \quad (A)$$

wherein:
$Cp^A$ is a cyclopentadienyl group with an alkenyl substituent; $Cp^B$ is a fluorenyl group; and each R independently is H, a $C_1$ to $C_{36}$ hydrocarbyl group, or a $C_1$ to $C_{36}$ hydrocarbylsilyl group.

Embodiment 2. A metallocene compound having the formula:

$$\begin{array}{c}R\\ \diagdown\\ R\diagup\end{array} N-B\begin{array}{c}Cp^A\\ \diagdown\\ \diagup\\ Cp^B\end{array}M\begin{array}{c}X\\ \diagdown\\ X\end{array}\;; \quad (I)$$

wherein:
M is Ti, Zr, or Hf; each X independently is a monoanionic ligand; $Cp^A$ is a cyclopentadienyl group with an alkenyl substituent; $Cp^B$ is a fluorenyl group; and each R independently is H, a $C_1$ to $C_{36}$ hydrocarbyl group, or a $C_1$ to $C_{36}$ hydrocarbylsilyl group.

Embodiment 3. The compound defined in embodiment 1 or 2, wherein $Cp^A$ is a cyclopentadienyl group with an alkenyl substituent, and $Cp^B$ is a fluorenyl group that does not have an alkenyl substituent.

Embodiment 4. The compound defined in embodiment 1 or 2, wherein $Cp^A$ is a cyclopentadienyl group with an alkenyl substituent, and $Cp^B$ is a fluorenyl group with an alkenyl substituent.

Embodiment 5. The compound defined in any one of embodiments 1-4, wherein $Cp^A$ is a cyclopentadienyl group with one alkenyl substituent.

Embodiment 6. The compound defined in any one of embodiments 1-5, wherein the alkenyl substituent is any alkenyl group disclosed herein, e.g., a $C_2$ to $C_{18}$ alkenyl group.

Embodiment 7. The compound defined in any one of embodiments 1-6, wherein the alkenyl substituent is an ethenyl group, a propenyl group, a butenyl group, a pentenyl group, a hexenyl group, a heptenyl group, an octenyl group, a nonenyl group, or a decenyl group.

Embodiment 8. The compound defined in any one of embodiments 1-6, wherein the alkenyl substituent is a $C_3$ to $C_{12}$ linear alkenyl group.

Embodiment 9. The compound defined in any one of embodiments 1-6, wherein the alkenyl substituent is a $C_3$ to $C_8$ terminal alkenyl group (e.g., a $C_3$ to $C_6$ terminal alkenyl group).

Embodiment 10. The compound defined in any one of embodiments 1-9, wherein $Cp^A$ contains a substituent (one or more) in addition to the alkenyl substituent, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Embodiment 11. The compound defined in any one of embodiments 1-10, wherein $Cp^B$ contains a substituent (one or more), e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Embodiment 12. The compound defined in embodiment 10 or 11, wherein the substituent (or each substituent independently) is H or a $C_1$ to $C_{18}$ hydrocarbyl group.

Embodiment 13. The compound defined in embodiment 10 or 11, wherein the substituent (or each substituent independently) is H, $C_1$, $CF_3$, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, a naphthyl group, a trimethylsilyl group, a triisopropylsilyl group, a triphenylsilyl group, an allyldimethylsilyl group, or a 1-methylcyclohexyl group.

Embodiment 14. The compound defined in embodiment 10 or 11, wherein the substituent (or each substituent independently) is a $C_1$ to $C_6$ linear or branched alkyl group (e.g., a tert-butyl group).

Embodiment 15. The compound defined in any one of embodiments 1-14, wherein each R independently is H or any $C_1$ to $C_{18}$ hydrocarbyl group or $C_1$ to $C_{18}$ hydrocarbylsilyl group disclosed herein.

Embodiment 16. The compound defined in any one of embodiments 1-14, wherein each R independently is a methyl group, an ethyl group, a propyl group, a butyl group, a pentyl group, a hexyl group, a heptyl group, an octyl group, a nonyl group, a decyl group, a phenyl group, a tolyl group, a benzyl group, a naphthyl group, a trimethylsilyl group, a triisopropylsilyl group, a triphenylsilyl group, an allyldimethylsilyl group, or a 1-methylcyclohexyl group.

Embodiment 17. The compound defined in any one of embodiments 1-14, wherein each R independently is a $C_1$ to $C_6$ linear or branched alkyl group (e.g., an isopropyl group).

Embodiment 18. The compound defined in any one of embodiments 2-17, wherein M is Ti.

Embodiment 19. The compound defined in any one of embodiments 2-17, wherein M is Zr.

Embodiment 20. The compound defined in any one of embodiments 2-17, wherein M is Hf.

Embodiment 21. The compound defined in any one of embodiments 2-20, wherein each X independently is any monoanionic ligand disclosed herein.

Embodiment 22. The compound defined in any one of embodiments 2-21, wherein each X independently is H, $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $OBR^1_2$, or $OSO_2R^1$, wherein $R^1$ is a $C_1$ to $C_{36}$ hydrocarbyl group.

Embodiment 23. The compound defined in any one of embodiments 2-22, wherein each X independently is any halide or $C_1$ to $C_{18}$ hydrocarbyl group disclosed herein.

Embodiment 24. The compound defined in any one of embodiments 2-23, wherein each X is Cl.

Embodiment 25. A catalyst composition comprising the metallocene compound defined in any one of embodiments 2-24, an activator, and an optional co-catalyst.

Embodiment 26. The composition defined in embodiment 25, wherein the activator comprises any activator disclosed herein.

Embodiment 27. The composition defined in embodiment 25 or 26, wherein the activator comprises an aluminoxane compound, an organoboron or organoborate compound, an ionizing ionic compound, or any combination thereof.

Embodiment 28. The composition defined in any one of embodiments 25-27, wherein the activator comprises an aluminoxane compound.

Embodiment 29. The composition defined in any one of embodiments 25-27, wherein the activator comprises an organoboron or organoborate compound.

Embodiment 30. The composition defined in any one of embodiments 25-27, wherein the activator comprises an ionizing ionic compound.

Embodiment 31. The composition defined in embodiment 25 or 26, wherein the activator comprises an activator-support, the activator-support comprising any solid oxide treated with an electron-withdrawing anion disclosed herein.

Embodiment 32. The composition defined in embodiment 31, wherein the solid oxide comprises any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Embodiment 33. The composition defined in embodiment 31, wherein the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

Embodiment 34. The composition defined in embodiment 31, wherein the activator-support comprises fluorided alumina, sulfated alumina, fluorided silica-alumina, sulfated silica-alumina, fluorided silica-coated alumina, sulfated silica-coated alumina, or any combination thereof.

Embodiment 35. The composition defined in embodiment 31, wherein the activator-support comprises a fluorided solid oxide, a sulfated solid oxide, or any combination thereof.

Embodiment 36. The composition defined in embodiment 31, wherein the activator-support further comprises any metal or metal ion disclosed herein, e.g., zinc, nickel, vanadium, titanium, silver, copper, gallium, tin, tungsten, molybdenum, zirconium, or any combination thereof.

Embodiment 37. The composition defined in embodiment 25 or 26, wherein the activator comprises an activator-support, the activator-support comprising a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

Embodiment 38. The composition defined in any one of embodiments 25-37, wherein the catalyst composition comprises a co-catalyst, e.g., any co-catalyst disclosed herein.

Embodiment 39. The composition defined in any one of embodiments 25-38, wherein the co-catalyst comprises an organoaluminum compound, an organozinc compound, an organomagnesium compound, an organolithium compound, or any combination thereof.

Embodiment 40. The composition defined in any one of embodiments 25-39, wherein the co-catalyst comprises an organoaluminum compound.

Embodiment 41. The composition defined in embodiment 40, wherein the organoaluminum compound comprises any organoaluminum compound disclosed herein, e.g., trimethylaluminum, triethylaluminum, triisobutylaluminum, etc., or combinations thereof.

Embodiment 42. The composition defined in any one of embodiments 31-41, wherein the catalyst composition is substantially free of aluminoxane compounds, organoboron or organoborate compounds, ionizing ionic compounds, or combinations thereof.

Embodiment 43. The composition defined in any one of embodiments 31-41, wherein the co-catalyst comprises an aluminoxane compound, an organoboron or organoborate compound, an ionizing ionic compound, an organoaluminum compound, an organozinc compound, an organomagnesium compound, an organolithium compound, or any combination thereof.

Embodiment 44. The composition defined in any one of embodiments 25-43, wherein the catalyst composition comprises any compound having formula (I) disclosed herein.

Embodiment 45. The composition defined in any one of embodiments 25-44, wherein the catalyst composition comprises only one compound having formula (I).

Embodiment 46. The composition defined in any one of embodiments 25-45, wherein the catalyst composition is produced by a process comprising contacting the metallocene compound and the activator.

Embodiment 47. The composition defined in any one of embodiments 25-46, wherein the catalyst composition is produced by a process comprising contacting, in any order, the metallocene compound, the activator, and the co-catalyst.

Embodiment 48. The composition defined in any one of embodiments 25-47, wherein a catalyst activity of the catalyst composition is in any range disclosed herein, e.g., greater than about 100,000 grams, greater than about 200,000 grams, greater than about 500,000 grams, etc., of ethylene polymer per gram of metallocene compound per hour, under slurry polymerization conditions, with a triisobutylaluminum co-catalyst, using isobutane as a diluent, and with a polymerization temperature of 80° C. and a reactor pressure of 390 psig.

Embodiment 49. An olefin polymerization process, the process comprising contacting the catalyst composition defined in any one of embodiments 25-48 with an olefin monomer and an optional olefin comonomer in a polymerization reactor system under polymerization conditions to produce an olefin polymer.

Embodiment 50. The process defined in embodiment 49, wherein the olefin monomer comprises any olefin monomer disclosed herein, e.g., any $C_2$-$C_{20}$ olefin.

Embodiment 51. The process defined in embodiment 49 or 50, wherein the olefin monomer and the optional olefin comonomer independently comprise a $C_2$-$C_{20}$ alpha-olefin.

Embodiment 52. The process defined in any one of embodiments 49-51, wherein the olefin monomer comprises ethylene.

Embodiment 53. The process defined in any one of embodiments 49-52, wherein the catalyst composition is contacted with ethylene and an olefin comonomer comprising a $C_3$-$C_{10}$ alpha-olefin.

Embodiment 54. The process defined in any one of embodiments 49-53, wherein the catalyst composition is contacted with ethylene and an olefin comonomer comprising 1-butene, 1-hexene, 1-octene, or a mixture thereof.

Embodiment 55. The process defined in any one of embodiments 49-51, wherein the olefin monomer comprises propylene.

Embodiment 56. The process defined in any one of embodiments 49-55, wherein the polymerization reactor system comprises a batch reactor, a slurry reactor, a gas-phase reactor, a solution reactor, a high pressure reactor, a tubular reactor, an autoclave reactor, or a combination thereof.

Embodiment 57. The process defined in any one of embodiments 49-56, wherein the polymerization reactor system comprises a slurry reactor, a gas-phase reactor, a solution reactor, or a combination thereof.

Embodiment 58. The process defined in any one of embodiments 49-57, wherein the polymerization reactor system comprises a loop slurry reactor.

Embodiment 59. The process defined in any one of embodiments 49-58, wherein the polymerization reactor system comprises a single reactor.

Embodiment 60. The process defined in any one of embodiments 49-58, wherein the polymerization reactor system comprises 2 reactors.

Embodiment 61. The process defined in any one of embodiments 49-58, wherein the polymerization reactor system comprises more than 2 reactors.

Embodiment 62. The process defined in any one of embodiments 49-61, wherein the olefin polymer comprises any olefin polymer disclosed herein.

Embodiment 63. The process defined in any one of embodiments 49-62, wherein the olefin polymer is an ethylene homopolymer, an ethylene/1-butene copolymer, an ethylene/1-hexene copolymer, or an ethylene/1-octene copolymer.

Embodiment 64. The process defined in any one of embodiments 49-63, wherein the olefin polymer is an ethylene/1-hexene copolymer.

Embodiment 65. The process defined in any one of embodiments 49-62, wherein the olefin polymer is a polypropylene homopolymer or a propylene-based copolymer.

Embodiment 66. The process defined in any one of embodiments 49-65, wherein the polymerization conditions comprise a polymerization reaction temperature in a range from about 60° C. to about 120° C. and a reaction pressure in a range from about 200 to about 1000 psig (about 1.4 to about 6.9 MPa).

Embodiment 67. The process defined in any one of embodiments 49-66, wherein the polymerization conditions are substantially constant, e.g., for a particular polymer grade.

Embodiment 68. The process defined in any one of embodiments 49-67, wherein no hydrogen is added to the polymerization reactor system.

Embodiment 69. The process defined in any one of embodiments 49-67, wherein hydrogen is added to the polymerization reactor system.

Embodiment 70. The process defined in any one of embodiments 49-67, wherein the ratio of Mw/Mn of the olefin polymer increases as the amount of hydrogen added to the polymerization reactor system increases, e.g., the Mw/Mn ratio of the polymer produced by the process in pressure of zero added hydrogen is less than the Mw/Mn of a polymer produced by the process in the presence of hydrogen at a molar ratio of $H_2$:olefin monomer of 0.1:1; the Mw/Mn ratio of the polymer produced by the process in the presence of hydrogen at a molar ratio of $H_2$:olefin monomer equal to 0.1:1 is less than the Mw/Mn of a polymer produced by the process in the presence of hydrogen at a molar ratio of $H_2$:olefin monomer of 0.25:1; etc., under the same polymerization conditions.

Embodiment 71. The process defined in any one of embodiments 49-70, wherein the olefin polymer has a density in any range disclosed herein, e.g., from about 0.89 to about 0.96, from about 0.91 to about 0.96, from about 0.92 to about 0.95 g/cm$^3$, etc.

Embodiment 72. The process defined in any one of embodiments 49-71, wherein the olefin polymer has less than about 0.01 long chain branches (LCB) per 1000 total carbon atoms, e.g., less than about 0.008 LCB per 1000 total carbon atoms, less than about 0.005 LCB per 1000 total carbon atoms, less than about 0.003 LCB per 1000 total carbon atoms, etc.

Embodiment 73. The process defined in any one of embodiments 49-72, wherein the olefin polymer has a ratio of Mw/Mn in any range disclosed herein, e.g., from about 2 to about 12, from about 2 to about 8, from about 2 to about 5, from about 2 to about 4, etc.

Embodiment 74. The process defined in any one of embodiments 49-73, wherein the olefin polymer has a ratio of Mz/Mw in any range disclosed herein, e.g., from about 1.5 to about 5, from about 1.5 to about 3, from about 1.8 to about 2.8, etc.

Embodiment 75. The process defined in any one of embodiments 49-74, wherein the olefin polymer has a conventional comonomer distribution, e.g., the number of short chain branches (SCB) per 1000 total carbon atoms at Mn is greater than Mw and/or the number of SCB per 1000 total carbon atoms at Mn is greater than at Mz, etc.

Embodiment 76. The process defined in any one of embodiments 49-74, wherein the olefin polymer has a substantially flat comonomer distribution.

Embodiment 77. The process defined in any one of embodiments 49-76, wherein the olefin polymer (e.g., an ethylene/1-hexene copolymer) has a decrease in density in any range disclosed herein, based on an increase in comonomer:monomer molar ratio (e.g., 1-hexene:ethylene molar ratio) from 0.034 to 0.068, e.g., a decrease in density of at least about 0.002 g/cm$^3$ (up to about 0.009-0.010 g/cm$^3$), at least about 0.003 g/cm$^3$, at least about 0.004 g/cm$^3$, at least about 0.005 g/cm$^3$, etc.

Embodiment 78. An olefin polymer produced by the olefin polymerization process defined in any one of embodiments 49-77.

Embodiment 79. An article comprising the olefin polymer defined in embodiment 78.

Embodiment 80. A method or forming or preparing an article of manufacture comprising an olefin polymer, the method comprising (i) performing the olefin polymerization process defined in any one of embodiments 49-77 to produce an olefin polymer, and (ii) forming the article of manufacture comprising the olefin polymer, e.g., via any technique disclosed herein.

Embodiment 81. The article defined in any one of embodiments 79-80, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

I claim:

1. An olefin polymerization process, the process comprising:
    contacting a catalyst composition with an olefin monomer and an optional olefin comonomer in a polymerization reactor system under polymerization conditions to produce an olefin polymer, wherein the catalyst composition comprises a metallocene compound, an activator, and an optional co-catalyst,
    wherein the metallocene compound has the formula:

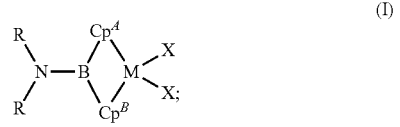

(I)

wherein:
M is Ti, Zr, or Hf;
each X independently is a monoanionic ligand;
$Cp^A$ is a cyclopentadienyl group with an alkenyl substituent;
$Cp^B$ is a fluorenyl group; and
each R independently is H, a $C_1$ to $C_{36}$ hydrocarbyl group, or a $C_1$ to $C_{36}$ hydrocarbylsilyl group.

2. The process of claim 1, wherein the catalyst composition comprises an organoaluminum co-catalyst.

3. The process of claim 1, wherein the activator comprises a fluorided solid oxide and/or a sulfated solid oxide.

4. The process of claim 1, wherein the activator comprises an aluminoxane compound, an organoboron or organoborate compound, an ionizing ionic compound, or any combination thereof.

5. The process of claim 1, wherein the activator comprises an activator-support, the activator-support comprising a solid oxide treated with an electron-withdrawing anion.

6. The process of claim 1, wherein:
M is Zr or Hf;
each X independently is a halide or a $C_1$ to $C_{18}$ hydrocarbyl group;
each R independently is H or a $C_1$ to $C_{18}$ hydrocarbyl group;
the polymerization reactor system comprises a slurry reactor, gas-phase reactor, solution reactor, or a combination thereof; and
the olefin monomer comprises ethylene, and the olefin comonomer comprises 1-butene, 1-hexene, 1-octene, or a mixture thereof.

7. The process of claim 1, wherein the process is capable of decreasing a density of an olefin copolymer by at least about 0.003 g/cm³, based on an increase in comonomer:monomer molar ratio from 0.034:1 to 0.068:1.

8. The process of claim 1, wherein the olefin polymer is an ethylene polymer characterized by less than about 0.005 long chain branches (LCB) per 1000 total carbon atoms.

9. The process of claim 1, wherein the olefin polymer is an ethylene/α-olefin copolymer characterized by a conventional comonomer distribution or a substantially flat comonomer distribution.

10. The process of claim 1, wherein the ratio of Mw/Mn of the olefin polymer increases as the amount of hydrogen added to the polymerization reactor system increases.

11. The process of claim 1, wherein:
M is Zr or Hf;
each X independently is a halide or a $C_1$ to $C_{18}$ hydrocarbyl group;
$Cp^B$ is a substituted fluorenyl group; and
each R independently is H or a $C_1$ to $C_{18}$ hydrocarbyl group.

12. The process of claim 1, wherein:
M is Zr or Hf;
each X independently is Cl, methyl, phenyl, or benzyl;
$Cp^A$ is a cyclopentadienyl group with only one alkenyl substituent;
$Cp^B$ is a substituted fluorenyl group; and
each R independently is a $C_1$ to $C_6$ alkyl group.

13. The process of claim 12, wherein the activator comprises an activator-support, the activator-support comprising a solid oxide treated with an electron-withdrawing anion.

14. The process of claim 12, wherein the activator comprises an aluminoxane compound, an organoboron or organoborate compound, an ionizing ionic compound, or any combination thereof.

15. The process of claim 1, wherein the catalyst composition comprises an organoaluminum co-catalyst, and wherein the activator comprises an activator-support, the activator-support comprising fluorided alumina, sulfated alumina, fluorided silica-alumina, sulfated silica-alumina, fluorided silica-coated alumina, sulfated silica-coated alumina, or any combination thereof.

16. The process of claim 1, wherein a catalyst activity of the catalyst composition is greater than about 100,000 grams of ethylene polymer per gram of the metallocene compound per hour, under slurry polymerization conditions, with a triisobutylaluminum co-catalyst, using isobutane as a diluent, and with a polymerization temperature of 80° C. and a reactor pressure of 390 psig.

17. The process of claim 1, wherein:
the activator comprises a fluorided solid oxide and/or a sulfated solid oxide;
the polymerization reactor system comprises a slurry reactor, gas-phase reactor, solution reactor, or a combination thereof; and
the catalyst composition is contacted with ethylene and an olefin comonomer comprising 1-butene, 1-hexene, 1-octene, or a mixture thereof.

18. The process of claim 17, wherein:
M is Zr or Hf;
each X independently is a halide or a $C_1$ to $C_{18}$ hydrocarbyl group; and
each R independently is H or a $C_1$ to $C_{18}$ hydrocarbyl group.

19. The process of claim 17, wherein:
M is Zr or Hf;
each X independently is Cl, methyl, phenyl, or benzyl;
each R independently is a $C_1$ to $C_6$ alkyl group; and
the polymerization reactor system comprises a loop slurry reactor.

* * * * *